US012642825B2

(12) United States Patent
Jang et al.

(10) Patent No.: US 12,642,825 B2
(45) Date of Patent: Jun. 2, 2026

(54) COMPOSITION FOR TREATING RESPIRATORY DISEASES OR INFLAMMATORY DISEASES CAUSED BY FINE DUST STIMULATION, CONTAINING LACTIC ACID BACTERIA

(71) Applicant: GREEN CROSS WELLBEING CORPORATION, Seoul (KR)

(72) Inventors: Minjung Jang, Seoul (KR); Gyeongeun Hong, Seoul (KR); Gideok Park, Seoul (KR); Jaeyoung Kim, Seoul (KR); Hyunsu Kim, Seoul (KR); Yongpil Hwang, Jinju-si (KR)

(73) Assignee: GREEN CROSS WELLBEING CORPORATION, Seoul (KR)

( * ) Notice: Subject to any disclaimer, the term of this patent is extended or adjusted under 35 U.S.C. 154(b) by 671 days.

(21) Appl. No.: 17/927,167

(22) PCT Filed: Apr. 23, 2021

(86) PCT No.: PCT/KR2021/005196
§ 371 (c)(1),
(2) Date: Nov. 22, 2022

(87) PCT Pub. No.: WO2021/235713
PCT Pub. Date: Nov. 25, 2021

(65) Prior Publication Data
US 2023/0201277 A1     Jun. 29, 2023

(30) Foreign Application Priority Data

May 22, 2020     (KR) ........................ 10-2020-0061851

(51) Int. Cl.
*A61K 35/747*     (2015.01)
*A23L 33/135*     (2016.01)
(Continued)

(52) U.S. Cl.
CPC .......... *A61K 35/744* (2013.01); *A23L 33/135* (2016.08); *A61P 11/00* (2018.01); *C12N 1/205* (2021.05)

(58) Field of Classification Search
None
See application file for complete search history.

(56) References Cited

U.S. PATENT DOCUMENTS

2008/0131413 A1     6/2008     Herz et al.
2012/0201798 A1     8/2012     Kekkonen et al.
(Continued)

FOREIGN PATENT DOCUMENTS

CN     101575582 A     11/2009
CN     107619811 A     1/2018
(Continued)

OTHER PUBLICATIONS

GenBank CP025471, *Pediococcus acidilactici* strain PB22 chromosome, complete genome, published 2018 (Year: 2018).*
(Continued)

*Primary Examiner* — Thane Underdahl
*Assistant Examiner* — Mary A Crum
(74) *Attorney, Agent, or Firm* — Sughrue Mion, PLLC

(57)     ABSTRACT

Novel strains of *Lactobacillus plantarum* GCWB1001 deposited as accession number KCCM12698P, *Pediococcus acidilactici* GCWB1085 deposited as accession number KCCM12699P, or *Lactobacillus rhamnosus* GCWB1156 deposited as accession number KCCM12700P are disclosed. The novel strains have the excellent effect of treating or alleviating respiratory diseases. Additionally, provided are a pharmaceutical composition, a health functional food composition, and probiotics, all of which have the effect of
(Continued)

$\#P < 0.001$ vs. normal group. $*P < 0.001$ vs. ConA10μg/ml+DEP200μg/ml treated group. $**P < 0.01$ vs. ConA10μg/ml+DEP200μg/ml treated group.

treating or alleviating inflammatory diseases or respiratory diseases, containing any one of the novel strains.

10 Claims, 16 Drawing Sheets

Specification includes a Sequence Listing.

(51) Int. Cl.

| | | |
|---|---|---|
| *A61K 35/744* | (2015.01) | |
| *A61P 11/00* | (2006.01) | |
| *C12N 1/205* | (2026.01) | |

(56) References Cited

U.S. PATENT DOCUMENTS

| | | |
|---|---|---|
| 2019/0365832 A1 | 12/2019 | Lin et al. |
| 2021/0054467 A1 | 2/2021 | Kim et al. |
| 2022/0323515 A1 | 10/2022 | Kim et al. |
| 2023/0355690 A1 | 11/2023 | Kim et al. |

FOREIGN PATENT DOCUMENTS

| | | | | |
|---|---|---|---|---|
| CN | 110494551 A | 11/2019 | | |
| CN | 110721204 A | 1/2020 | | |
| JP | 2018-538009 A | 12/2018 | | |
| KR | 10-2012-0106943 A | 9/2012 | | |
| KR | 10-1178217 B1 | 9/2012 | | |
| KR | 10-2013-0046897 A | 5/2013 | | |
| KR | 10-1277447 B1 | 6/2013 | | |
| KR | 10-1802447 B1 | 11/2017 | | |
| KR | 10-2018-0037693 A | 4/2018 | | |
| KR | 10-2018-0098729 A | 9/2018 | | |
| KR | 10-1912258 B1 | 10/2018 | | |
| KR | 10-1933467 B1 | 2/2019 | | |
| KR | 10-2019-0048613 A | 5/2019 | | |
| KR | 10-1979761 B1 | 5/2019 | | |
| KR | 10-2019-0068026 A | 6/2019 | | |
| KR | 10-2001992 B1 | 7/2019 | | |
| KR | 10-2021881 B1 | 9/2019 | | |
| KR | 10-2021883 B1 | 9/2019 | | |
| KR | 20190118985 A | * | 10/2019 | ................ A61P 3/04 |
| KR | 10-2049970 B1 | 11/2019 | | |
| KR | 10-2098991 B1 | 4/2020 | | |
| KR | 10-2020-0054594 A | 5/2020 | | |
| KR | 10-2165929 B1 | 10/2020 | | |
| WO | 2018143678 A1 | 8/2018 | | |
| WO | 2018/191073 A1 | 10/2018 | | |
| WO | 2019/088421 A1 | 5/2019 | | |

OTHER PUBLICATIONS

Du, Tingfeng, et al. "The beneficial role of probiotic Lactobacillus in respiratory diseases." Frontiers in immunology 13 (2022): 908010. (Year: 2022).*

Lan, Huan, et al. "Oral administration of Lactobacillus plantarum CQPC11 attenuated the airway inflammation in an ovalbumin (OVA)-induced Balb/c mouse model of asthma." Journal of Food Biochemistry 46.2 (2022): e14036. (Year: 2022).*

Moratz et al., "Anti-Inflammatory Effects of Lactobacillus Rahmnosus and Bifidobacterium Breve on Cigarette Smoke Activated Human Macrophages", Plos One, Aug. 28, 2015, vol. 10, No. 8, e0136455, pp. 1-17 (17 pages total).

Wang et al., "Oral administration of Lactobacillus paracasei L9 attenuates PM2.5-induced enhancement of airway hyperresponsiveness and allergic airway response in murine model of asthma", Plos One, Feb. 15, 2017, vol. 12, No. 2, e0171721, pp. 1-18 (18 pages total).

"*Pediococcus acidilactici* gene for 16S ribosomal RNA, partial sequence, strain: JCM 8797", GenBank Accession No. LC097074. 1, Nov. 17, 2015 (1 page total).

"*Lactobacillus rhamnosus* strain IDCC 3201 chromosome", GenBank Accession No. CP045531.1, Oct. 31, 2019 (635 pages total).

Korea Food Research Institute, "Probiotics' helps respiratory health", Press Release, Mar. 17, 2020 (12 pages total).

International Search Report issued Aug. 23, 2021 in International Application No. PCT/KR2021/005196.

"Pediococcus acidilactici GWCB1085", Accession No. KCCM12699P, Budapest Treaty of the International Recognition of the Deposit of Microorganisms for the Purposes of Patent Procedure, Apr. 17, 2020 (1 page total).

"Lactobacillus plantarum GWCB1001", Accession No. KCCM12698P, Budapest Treaty of the International Recognition of the Deposit of Microorganisms for the Purposes of Patent Procedure, Apr. 17, 2020 (1 page total).

"Lactobacillus rhamnosus GWCB1156", Accession No. KCCM12700P, Budapest Treaty of the International Recognition of the Deposit of Microorganisms for the Purposes of Patent Procedure, Apr. 17, 2020 (1 page total).

Sun Woo Jin, et al., "Lactic Acid Bacteria Ameliorate Diesel Exhaust Particulate Matter-Exacerbated Allergic Inflammation in a Murine Model of Asthma", Life, 2020, vol. 10, 260, XP093176282 (16 pages).

Extended European Search Report dated Jul. 8, 2024 in Application No. 21809863.0.

* cited by examiner

Measurement of transcriptional regulator activity (iNOS-Luc)

P < 0.001 vs. normal group. *P < 0.001 vs. LPS10ng/ml group. P < 0.01 vs. LPS10ng/ml+DEP200μg/ml treated group. *P < 0.01 vs. LPS10ng/ml+DEP200μg/ml treated group.

P < 0.001 vs. normal group. *P < 0.001 vs. LPS10ng/mℓ +DEP200µg/mℓ treated group.

P < 0.001 vs normal group. *P < 0.001 vs OVA plus DEP-treated group.

P < 0.001 vs normal group. *P < 0.001 vs OVA plus DEP-treated group.

P < 0.001 vs normal group. *P < 0.001 vs OVA plus DEP-treated group. P < 0.01 vs OVA plus DEP-treated group. *P < 0.05 vs OVA plus DEP-treated group.

P < 0.001 vs normal group. *P < 0.001 vs OVA plus DEP-treated group.

P < 0.001 vs normal group. *P < 0.001 vs OVA plus DEP-treated group.

P < 0.001 vs normal group. *P < 0.001 vs OVA plus DEP-treated group.

P < 0.001 vs normal group. *P < 0.001 vs OVA plus DEP-treated group.

SEQUENCE LISTING

<160> NUMBER OF SEQ ID NOS: 5

<210> SEQ ID NO 1
<211> LENGTH: 1434
<212> TYPE: DNA
<213> ORGANISM: Lactobacillus plantarum

<400> SEQUENCE: 1

```
ggtcgtacga actctgtgta ttgattggtg cttgcatcat gatttacatt tgcagtgagt     60
ggcgaactgg tgagtaacac gtgggaaacc tgcccagaag cggggataa cacctggaaa     120 cagatgctaa taccgcataa caacttggac cgcatggtcc gagtttgaaa gatggcttcg     180
gctatcactt ttggatggtc ccgcggcgta ttagctagat ggtggggtaa cggctcacca     240
tggcaatgat acgtagccga cctgagaggg taatcggcca cattgggact gagacacggc     300
ccaaactcct acgggaggca gcagtaggga atcttccaca atggacgaaa gtctgatgga     360
gcaacgccgc gtgagtgaag aagggtttcg gctcgtaaaa ctctgttgtt gaagaagaac     420
atatctgaga gtaactgttc aggtattgac ggtatttaac cagaaagcca cggctaacta     480
cgtgccagca gccgcggtaa tacgtaggtg gcaagcgttg tccggattta ttgggcgtaa     540
agcgagcgca ggcggttttt taagtctgat gtgaaagcct tcggctcaac cgaagaagtg     600
catcggaaac tgggaaactt gagtgcagaa gaggacagtg gaactccatg tgtagcggtg     660
aaatgcgtag atatatggaa gaacaccagt ggcgaaggcg ctgtctggt ctgtaactga     720 cgctgaggct cgaaagtatg ggtagcaaac aggattagat accctggtag tccataccgt     780
aaacgatgaa tgctaagtgt tggagggttt ccgcccttca gtgctgcagc taacgcatta     840
agcattccgc ctggggagta cggccgcaag gctgaaactc aaaggaattg acgggggccc     900
gcacaagcgg tggagcatgt ggtttaattc gaagctacgc gaagaacctt accaggtctt     960
gacatactat gcaaatctaa gagattagac gttcccttcg gggacatgga tacaggtggt     1020
gcatggttgt cgtcagctcg tgtcgtgaga tgttgggtta agtcccgcaa cgagcgcaac     1080
ccttattatc agttgccagc attaagttgg gcactctggt gagactgccg gtgacaaacc     1140
ggaggaaggt ggggatgacg tcaaatcatc atgcccctta tgacctgggc tacacacgtg     1200
ctacaatgga tggtacaacg agttgcgaac tcgcgagagt aagctaatct cttaaagcca     1260
ttctcagttc ggattgtagg ctgcaactcg cctacatgaa gtcggaatcg ctagtaatcg     1320
cggatcagca tgccgcggtg aatacgttcc cgggccttgt acacaccgcc cgtcacacca     1380
tgagagtttg taacacccaa agtcggtggg gtaacctttt aggaaccagc cgct          1434
```

<210> SEQ ID NO 2
<211> LENGTH: 1499
<212> TYPE: DNA
<213> ORGANISM: Pediococcus acidilactici
<400> SEQUENCE: 2

```
ctcaggatga acgctggcgg cgtgcctaat acatgcaagt cgaacgaact tccgttaatt     60
gatcaggacg tgcttgcact gaatgagatt ttaacacgaa gtgagtggcg gacgggtgag     120
taacacgtgg gtaacctgcc cagaagcagg ggataacacc tggaaacaga tgctaatacc     180
gtataacaga gaaaccgcc tggttttctt ttaaaagatg gctctgctat cacttctgga     240
tggacccgcg gcgcattagc tagttggtga ggtaacggct caccaaggcg atgatgcgta     300
gccgacctga gagggtaatc ggccacattg gactgagac acggcccaga ctcctacggg     360
aggcagcagt agggaatctt ccacaatgga cgcaagtctg atggagcaac gccgcgtgag     420
tgaagaaggg tttcggctcg taaagctctg ttgttaaaga agaacgtggg tgagagtaac     480
tgttcaccca gtgacggtat ttaaccagaa agccacggct aactacgtgc cagcagccgc     540
ggtaatacgt aggtggcaag cgttatccgg atttattggg cgtaaagcga gcgcaggcgg     600 tctttaagt ctaatgtgaa agccttcggc tcaaccgaag aagtgcattg gaaactggga     660
```

-continued

```
gacttgagtg cagaagagga cagtggaact ccatgtgtag cggtgaaatg cgtagatata    720
tggaagaaca ccagtggcga aggcggctgt ctggtctgta actgacgctg aggctcgaaa    780
gcatgggtag cgaacaggat tagataccct ggtagtccat gccgtaaacg atgattacta    840
agtgttggag ggtttccgcc cttcagtgct gcagctaacg cattaagtaa tccgcctggg    900
gagtacgacc gcaaggttga aactcaaaag aattgacggg gcccgcaca agcggtggag     960 catgtggttt aattcgaagc tacgcgaaga accttaccag gtcttgacat cttctgccaa   1020
cctaagagat taggcgttcc cttcggggac agaatgacag gtggtgcatg gttgtcgtca   1080
gctcgtgtcg tgagatgttg ggttaagtcc cgcaacgagc gcaaccctta ttactagttg   1140
ccagcattca gttgggcact ctagtgagac tgccggtgac aaaccggagg aaggtgggga   1200
cgacgtcaaa tcatcatgcc ccttatgacc tgggctacac acgtgctaca atggatggta   1260
caacgagttg cgaaaccgcg aggtttagct aatctcttaa aaccattctc agttcggact   1320
gtaggctgca actcgcctac acgaagtcgg aatcgctagt aatcgcggat cagcatgccg   1380
cggtgaatac gttcccgggc cttgtacaca ccgcccgtca caccatgaga gtttgtaaca   1440
cccaaagccg gtggggtaac cttttaggag ctagccgtct aaggtgggac agatgattta   1499
```

```
<210> SEQ ID NO 3
<211> LENGTH: 1188
<212> TYPE: DNA
<213> ORGANISM: Lactobacillus rhamnosus

<400> SEQUENCE: 3
```

```
gttgatcggc cacattggga ctgagacacg gcccaaactc ctacgggagg cagcagtagg     60
gaatcttcca caatggacgc aagtctgatg gagcaacgcc gcgtgagtga agaaggcttt    120
cgggtcgtaa aactctgttg ttggagaaga atggtcggca gagtaactgt tgtcggcgtg    180
acggtatcca accagaaagc cacggctaac tacgtgccag cagccgcggt aatacgtagg    240
tggcaagcgt tatccggatt tattgggcgt aaagcgagcg caggcggttt tttaagtctg    300
atgtgaaagc cctcggctta accgaggaag tgcatcggaa actgggaaac ttgagtgcag    360
aagaggacag tggaactcca tgtgtagcgg tgaaatgcgt agatatatgg aagaacacca    420
gtggcgaagg cggctgtctg gtctgtaact gacgctgagg ctcgaaagca tgggtagcga    480
acaggattag ataccctggt agtccatgcc gtaaacgatg aatgctaggt gttgagggt     540 ttccgccctt cagtgccgca gctaacgcat taagcattcc gcctggggag tacgaccgca    600
aggttgaaac tcaaaggaat tgacgggggc ccgcacaagc ggtggagcat gtggtttaat    660
tcgaagcaac gcgaagaacc ttaccaggtc ttgacatctt ttgatcacct gagagatcag    720
gtttcccctt cggggggcaaa atgacaggtg gtgcatggtt gtcgtcagct cgtgtcgtga    780
gatgttgggt taagtcccgc aacgagcgca acccttatga ctagttgcca gcatttagtt    840
gggcactcta gtaagactgc cggtgacaaa ccggaggaag gtggggatga cgtcaaatca    900
tcatgcccct tatgacctgg gctacacacg tgctacaatg gatggtacaa cgagttgcga    960
daccgcgagg tcaagctaat ctcttaaagc cattctcagt tcggactgta ggctgcaact   1020
cgcctacacg aagtcggaat cgctagtaat cgcggatcag cacgccgcgg tgaatacgtt   1080
cccgggcctt gtacacaccg cccgtcacac catgagagtt tgtaacaccc gaagccggtg   1140
gcgtaaccct tttagggagc gagccgtcta aggtgggaca aatgatta              1188
```

```
<210> SEQ ID NO 4
<211> LENGTH: 20
```

-continued

```
<212> TYPE: DNA
<213> ORGANISM: Artificial Sequence
<220> FEATURE:
<223> OTHER INFORMATION: primer 27F

<400> SEQUENCE: 4
agagtttgat cmtggctcag                                                  20

<210> SEQ ID NO 5
<211> LENGTH: 22
<212> TYPE: DNA
<213> ORGANISM: Artificial Sequence
<220> FEATURE:
<223> OTHER INFORMATION: primer 1492R

<400> SEQUENCE: 5
tacggytacc ttgttacgac tt                                               22
```

1

COMPOSITION FOR TREATING RESPIRATORY DISEASES OR INFLAMMATORY DISEASES CAUSED BY FINE DUST STIMULATION, CONTAINING LACTIC ACID BACTERIA

CROSS REFERENCE TO RELATED APPLICATIONS

This application is a National Stage of International Application No. PCT/KR2021/005196 filed on Apr. 23, 2021, claiming priority based on Korean Patent Application No. 10-2020-0061851 filed on May 22, 2020, the disclosures of which are incorporated by reference in their entireties.

INCORPORATION BY REFERENCE OF SEQUENCE LISTING

The content of the electronically submitted sequence listing, file name: Q282589_Sequence_Listing_As_Filed.txt; size: 6,452 bytes; and date of creation: Nov. 21, 2022, filed herewith, is incorporated herein by reference in its entirety.

TECHNICAL FIELD

The present disclosure relates to novel lactic acid bacteria having an effect of treating or preventing respiratory diseases or inflammatory diseases, and a pharmaceutical composition, a health functional food composition and probiotics comprising the same.

BACKGROUND ART

Fine dust is particulate matters of 10 μm or less that float in the air or is blown down, and according to the dust diameter classification, PM10 means particles smaller than 10/1,000 mm, and PM2.5 means particles smaller than 2.5/1,000 mm.

The fine dust is caused by directly emitting from anthropogenic sources such as workplace combustion and automobile fuel combustion, or generated by a secondary generation process in which materials such as sulfur oxides (SOx), nitrogen oxides (NOx), ammonia ($NH_3$), and volatile organic compounds (VOCs) react with water vapor in the air.

The fine dust is known to be able to penetrate directly into the alveoli or the brain without being filtered through the nasal mucosa when inhaled because of its fine particles, and is known to increase the prevalence rate and premature death rate of asthma and lung disease.

In particular, in 2013, the International Agency for Research on Cancer (IARC) under the World Health Organization (WHO) has classified the fine dust as a group 1 carcinogen, which was confirmed to cause cancer in humans, together with benzene and asbestos.

Living microorganisms that have a beneficial effect on the health of a host by improving an intestinal microbial environment of the host in the gastrointestinal tract of animals including humans are collectively called probiotics.

Lactic acid bacteria, which are a type of probiotics, serve to decompose fiber and complex proteins into important nutrients while coexisting in the digestive system of the human body. The lactic acid bacteria decompose carbohydrates and use the carbohydrates to produce lactic acid, which are anaerobic bacteria that proliferate well in places with little oxygen. The lactic acid bacteria are largely divided into five genera, *Streptococcus, Lactobacillus, Leuconostoc,* Bifidobacteria, and *Pediococcus.* Recently, therapeutic effects for various diseases using lactic acid bacteria have been confirmed, and the development of therapeutic agents using the lactic acid bacteria has been attempted.

Unlike respiratory and lung damage caused by conventional bacteria, temporary poisoning, or inflow of other substances into the airways, the fine dust cannot be eradicated by human immunity, and there is no method of forcibly discharging the fine dust when the fine dust is entered through the respiratory tract. Also, since it cannot be known exactly when and what problems will occur due to such damage, there is an urgent need for new therapeutic agents capable of preventing, alleviating, treating, or improving the damage to the airways and lungs induced by the fine dust, and thereby treating respiratory diseases induced by the fine dust.

DISCLOSURE

Technical Problem

It is an object of the present disclosure to provide a novel *Lactobacillus plantarum* GCWB1001 strain deposited as accession number KCCM12698P, a *Lactobacillus rhamnosus* GCWB1156 strain deposited as accession number KCCM12700P, a *Pediococcus acidilactici* GCWB1085 deposited as accession number KCCM12699P, and a composition comprising the same for preventing or treating inflammatory diseases or respiratory diseases.

Technical Solution

In order to achieve the object, the present disclosure provides a *Lactobacillus plantarum* GCWB1001 strain deposited as accession number KCCM12698P.

The present disclosure provides a *Lactobacillus rhamnosus* GCWB1156 strain deposited as accession number KCCM12700P.

The present disclosure provides a *Pediococcus acidilactici* GCWB1085 strain deposited as accession number KCCM12699P.

In addition, the present disclosure provides a pharmaceutical composition for preventing or treating inflammatory diseases or respiratory diseases including a *Lactobacillus plantarum* GCWB1001 strain deposited as accession number KCCM12698P, a *Lactobacillus rhamnosus* GCWB1156 strain deposited as accession number KCCM12700P, or a *Pediococcus acidilactici* GCWB1085 strain deposited as accession number KCCM12699P, one selected from a spray-dried product, a freeze-dried product, a vacuum dried product, a drum dried product, or a crushed product of the strains, or any one of a culture of the strains, and a concentrate, a paste and a dilution of the culture.

In addition, the present disclosure provides a health functional food composition for preventing or alleviating inflammatory diseases or respiratory diseases including a *Lactobacillus plantarum* GCWB1001 strain deposited as accession number KCCM12698P, a *Lactobacillus rhamnosus* GCWB1156 strain deposited as accession number KCCM12700P, or a *Pediococcus acidilactici* GCWB1085 strain deposited as accession number KCCM12699P, one selected from a spray-dried product, a freeze-dried product, a vacuum dried product, a drum dried product, or a crushed product of the strains, or any one of a culture of the strains, and a concentrate, a paste and a dilution of the culture.

In addition, the present disclosure provides probiotics including a *Lactobacillus plantarum* GCWB1001 strain deposited as accession number KCCM12698P, a *Lactobacillus rhamnosus* GCWB1156 strain deposited as accession number KCCM12700P, or a *Pediococcus acidilactici* GCWB1085 strain deposited as accession number KCCM12699P.

Advantageous Effects

According to an embodiment of the present disclosure, *Lactobacillus plantarum* GCWB1001 (KCCM12698P), *Lactobacillus rhamnosus* GCWB1156 (KCCM12700P), and *Pediococcus acidilactici* GCWB1085 (KCCM12699P) strains have an anti-inflammatory effect, and show an anti-tussive/expectorant effect and an effect of improving a lung function in chronic respiratory diseases in actual animal models.

According to an embodiment of the present disclosure, *Lactobacillus plantarum* GCWB1001 (KCCM12698P), *Lactobacillus rhamnosus* GCWB1156 (KCCM12700P), and *Pediococcus acidilactici* GCWB1085 (KCCM12699P) strains were isolated from kimchi, cheese, and infant feces, respectively, and each strain has not shown cytotoxicity in mouse lung macrophages (MH-S cell line), and has an effect of reducing the secretion of TNF-alpha and TGF-beta which are cytokines.

According to an embodiment of the present disclosure, all strains of the present disclosure not only reduced the production of nitric oxide (NO) and reactive oxygen species (ROS), which are inflammatory factors increased by fine dust, but also reduced the promoter activities of NF-kB, iNOS and COX2, which are inflammatory transcription factors.

According to an embodiment of the present disclosure, all strains of the present disclosure have effects of alleviating cough symptoms and an antitussive/expectorant effect in actual animal models, and also have shown an effect of alleviating various symptoms of a chronic respiratory disease animal model caused by fine dust.

Accordingly, as a result, *Lactobacillus plantarum* GCWB1001 (KCCM12698P), *Lactobacillus rhamnosus* GCWB1156 (KCCM12700P), and *Pediococcus acidilactici* GCWB1085 (KCCM12699P) strains of the present disclosure have shown the effect of alleviating, preventing, or treating inflammatory diseases or respiratory diseases.

BEST MODE

Figure 1:
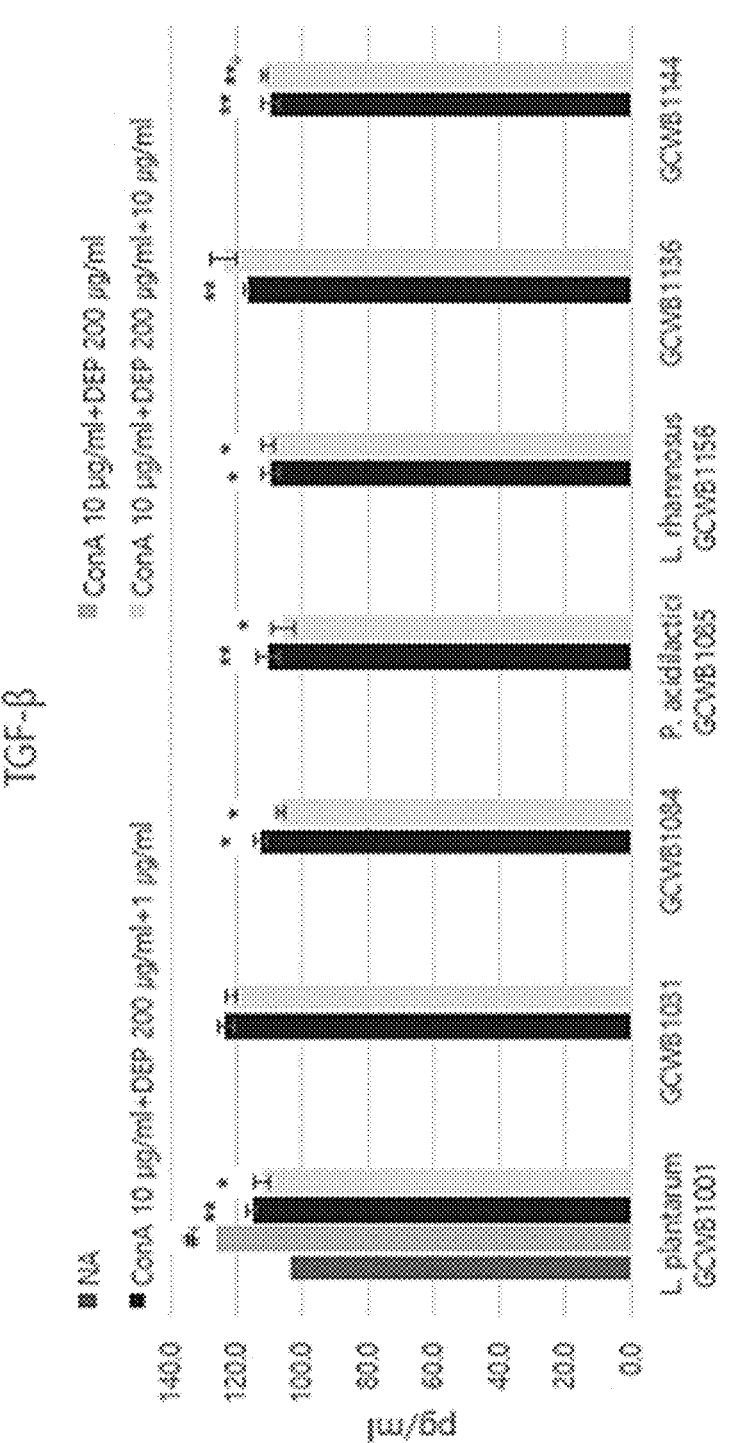
FIG. 1 is a graph showing the measurement of the TGF-β production amount by 7 types of strain samples in a mouse lung macrophage cell line (MH-S) (Experimental Example 1-2).

Hereinafter, the present disclosure will be described in detail.

All the technical terms used in the present disclosure, unless otherwise defined, have the meaning as commonly understood by those skilled in the art of the present disclosure. In addition, although preferred methods and samples are described herein, methods and samples similar or equivalent thereto are also included in the scope of the present disclosure.

The present disclosure relates to a *Lactobacillus plantarum* GCWB1001 strain deposited as accession number KCCM12698P.

The *Lactobacillus plantarum* GCWB1001, which is a novel strain, was named as described above and deposited with the Korean Culture Center of Microorganisms on Apr. 17, 2020. The accession number is KCCM12698P.

The strain may be isolated and identified from kimchi collected from each local region. The inventors of the present disclosure have isolated and identified various novel strains from kimchi collected from each local region, and confirmed that a *Lactobacillus plantarum* GCWB1001 strain among the isolated and identified strains provides a remarkably excellent anti-inflammatory effect and a preventive or therapeutic effect on respiratory diseases by comparing it with conventionally known lactic acid bacteria, and then completed the present disclosure.

The present disclosure relates to a *Lactobacillus rhamnosus* GCWB1156 strain deposited as accession number KCCM12700P.

The *Lactobacillus rhamnosus* GCWB1156 strain, which is a novel strain, was named as described above and deposited with the Korean Culture Center of Microorganisms on Apr. 17, 2020. The accession number is KCCM12700P.

The strain may be isolated and identified from cheese collected from each local region. The inventors of the present disclosure have isolated and identified various novel strains from cheese collected from each local region, and confirmed that a *Lactobacillus rhamnosus* GCWB1156 strain among the isolated and identified strains provides a remarkably excellent anti-inflammatory effect and a preventive or therapeutic effect on respiratory diseases by comparing it with conventionally known lactic acid bacteria, and then completed the present disclosure.

The present disclosure relates to a *Pediococcus acidilactici* GCWB1085 strain deposited as accession number KCCM12699P.

The *Pediococcus acidilactici* GCWB1085, which is a novel strain, was named as described above and deposited with the Korean Culture Center of Microorganisms on Apr. 17, 2020. The accession number is KCCM12699P.

The strain may be isolated and identified from infant feces. The inventors of the present disclosure have isolated and identified various novel strains from infant feces, and confirmed that a *Pediococcus acidilactici* GCWB1085 strain among the isolated and identified strains provides a remarkably excellent anti-inflammatory effect and a preventive or therapeutic effect on respiratory diseases by comparing it with conventionally known lactic acid bacteria, and then completed the present disclosure.

That is, the *Lactobacillus plantarum* GCWB1001 strain, the *Lactobacillus rhamnosus* GCWB1156 strain, and the *Pediococcus acidilactici* GCWB1085 strain inhibited the activity of NO, ROS, and inflammatory transcriptional regulators (promoter activities of iNOS, COX2 and NF-kB) in the MH-S cell line, which is a mouse lung macrophage cell line treated with LPS and fine dust (DEP; diesel exhaust particles) which are inflammation-inducing substances.

It was also confirmed that the GCWB1001, GCWB1156 and GCWB1085 strains of the present disclosure have an anti-inflammatory effect by reducing the cytokine (TNF-alpha) secretion induced by LPS and DEP in the MH-S cell line.

Oxidative stress refers to a phenomenon in which the production of reactive oxygen species or reactive nitrogen species and an antioxidation defense mechanism are out of balance in biomolecules, cells, and tissues in vivo, and the production of reactive oxygen species or reactive nitrogen species becomes relatively excessive, which generally causes tissue damage.

Since these reactive oxygen species or active nitrogen species are chemically very unstable and highly reactive, they cause an inflammatory response around them and are involved as a major factor in tissue fibrosis by causing enzyme-catalyzed reaction in vivo, electron transfer in mitochondria, cell signaling system and gene expression, activation of transcription factors, and extensive oxidative damage to biomolecules, cells, tissues, etc. This oxidative damage causes various diseases in all tissues of the human body. Specifically, the oxidative damage has been not only known to be involved in the occurrence of cancer and the progression of the occurring cancer in tissues such as skin, kidney, heart, joint, lung, brain, blood vessel, intestinal tract, and eyes, but also known to play important role in almost all diseases such as cardiovascular disease, inflammation, fibrotic disease, and diabetes.

When macrophages are treated with inflammatory substances such as LPS, inflammatory mediators (oxidative stress) such as inflammatory cytokines (IL-6, TNF-alpha, IL-1beta, etc.) and NO are generated to cause an inflammatory response. NO is produced by induced nitric oxide synthase (iNOS), activates the NF-kB transcription factor as the inflammatory response occurs, and simultaneously accelerates the inflammatory response by producing prostaglandins (PGs) involved in the inflammatory response by cyclooxygenase-2 (COX-2).

Therefore, as the GCWB1001, GCWB1156 and GCWB1085 strains of the present disclosure inhibit all activities of NO and ROS that are inflammatory substances induced by LPS and DEP, TNF-alpha that is an inflammatory cytokine, and the inflammatory transcriptional regulators (iNOS, COX2 and NF-kB promoters), the strains have an anti-inflammatory effect of inhibiting inflammation.

The GCWB1001, GCWB1156 and GCWB1085 strains of the present disclosure inhibited coughing and increased expectoration in a citric acid-induced cough model.

Antitussives are a drug that relieves a cough regardless of the cause, and may be divided into centrally acting drugs and peripherally acting drugs according to a mechanism of action, in which the centrally acting drugs may be divided into narcotic drugs, narcotic derivatives and non-narcotic drugs. The representative narcotic drugs are codein, hydrocodone, morphine, etc., which have proven to have a limited cough inhibiting effect, but the results are inconsistent and at appropriate doses, there is a risk of drowsiness, constipation, digestive problems, and abuse or dependence. Among the peripherally acting antitussives, the most commonly used drug in Korea is Levodropropizine, which is considered to be effective by controlling the level of sensory neuropeptides in the airways. In addition, theobromine corresponds thereto.

The main ingredient of sputum consists of mucus, and the bronchial mucus is secreted from mucous cells and serous gland cells constituting the mucous glands and submucosal glands normally distributed in the bronchial mucosa. The mucus consists of 95% of water and the rest 5% of glycoproteins, lipids, minerals, and the like, and shows a sticky aspect because the glycoprotein structure is in the form of a gel with a double structure of a linear polymer. Expectorants for removing the sputum are divided into drugs that increase the water content of the sputum and mucolytics that reduce viscosity by breaking S—S bonds of the sputum protein. As these expectorants, cysteine derivatives such as N-acetylcysteine and carbocysteine are used, and these cysteine derivatives may have side effects such as bronchospasm when used for a long period of time. Therefore, there is a demand for the development of an expectorant with less side effects and toxicity and an excellent expectorant effect.

In addition, as an antitussive expectorant made of natural materials, an ivy leaf extract and Synatura, which is a combination of ivy leaves and a goldthread extract, are widely used.

The GCWB1001, GCWB1156 and GCWB1085 strains of the present disclosure reduce the number of coughs in the citric acid-induced cough model, and exhibit an antitussive/expectant effect, thereby improving symptoms of respiratory diseases.

Additionally, the strains of the present disclosure not only significantly reduced immune cells in a bronchoalveolar lavage fluid (BALF) in a chronic respiratory disease model using ovalbumin (OVA) and diesel exhaust particles (DEP), but also reduced the immune cells penetrating into the lung tissue, reduced OVA-specific IgE, and decreased TNF-alpha, IL-6, IL-1beta, IL-4, MCP-1 and IL-13, which are inflammatory cytokines in the BALF, and significantly increased IFN-gamma which is an anti-inflammatory cytokine.

Therefore, the GCWB1001, GCWB1156 and GCWB1085 strains of the present disclosure not only act as the antitussive/expectant as they are, but also inhibit the activity of MMP9 to block the BALF and the inflammatory cells in lung tissue, block the secretion of inflammatory cytokines, increase the secretion of anti-inflammatory cytokines, and reduce the amount of IgE immunoglobulin increased in allergy symptoms, thereby reducing allergic and inflammatory responses in the respiratory organs.

Representative respiratory diseases include asthma, pneumonia, chronic obstructive pulmonary disease, allergic rhinitis, acute chronic bronchitis, bronchiolitis, pharyngitis, tonsillitis, laryngitis, bronchiectasis, idiopathic pulmonary fibrosis, cystic fibrosis, emphysema, sequelae of pulmonary tuberculosis, lower respiratory tract infection, sinusitis, acute upper respiratory tract infection, allergic lung disease, and the like. The asthma is a chronic inflammation of the airways, especially the bronchi. Inflammation caused by the asthma may be exacerbated by a wide variety of factors, such as soot, allergens, cold wind, exercise, and respiratory infections, and persistent inflammation causes deformation of the airway and hyper-responsiveness of the airway.

In addition, respiratory diseases may be caused by respiratory infectious viruses. Types of viruses causing the respiratory diseases include adenovirus, vaccinia virus, herpes simplex virus, parainfluenza virus, rhinovirus, varicella Zoster Virus, measle virus, respiratory syncytial virus, Dengue virus, human immunodeficiency virus (HIV), influenza virus, coronavirus, severe acute respiratory syndrome associated virus (SARS-associated virus), middle east respiratory syndrome coronavirus (MERS-CoV), and the like.

The respiratory tract largely consists of mucous membranes and muscles called bronchial smooth muscles, and the mucous membranes have many glands to continuously secrete necessary secretions, and when the bronchial smooth muscles contract, the respiratory tract narrows. When an inflammatory response occurs due to a wide variety of factors such as soot, allergens, cold wind, exercise, and respiratory infections, the secretions from the glands further increase. The secretions secreted at this time are caused by an exudative reaction due to inflammation, and most of the secretions are sticky mucous secretions composed of a mixture of an inflammatory mediator and mucin.

The mucin usually performs a role in defending the living body, but in chronic inflammatory respiratory diseases such as asthma, COPD, and chronic bronchitis, overproduction or oversecretion of sticky secretions is observed. Abnormalities in the quantity and quality of the secretion act as a pathological factor, causing endotracheal occlusion and obstruction of air inflow into the airways due to secretion accumulation, and as a result, a paroxysmal cough and dyspnoea accompanied by wheezing are severe and during the paroxysm, a dry cough occurs and a feeling of chest pressure is felt. Lung damage caused by viral respiratory diseases is also considered to be caused by this mucin.

In a chronic respiratory disease animal model, the GCWB1001, GCWB1156 and GCWB1085 strains of the present disclosure inhibit the deposition of mucous proteins in lung tissue, reduce the activity of caspase 3, which is an apoptosis factor in the alveoli, lowered collagen deposition, and decreased the activity of MMP-9. The decrease in the activity of MMP-9 may prevent the deposition of inflammatory cells in the lung tissue, thereby ultimately preventing pulmonary fibrosis.

The pulmonary fibrosis is the last stage of respiratory diseases, in which the pathological and physiological processes are complex. In the early stage, a large amount of inflammatory cells infiltrate based on lung inflammation and the alveolar wall becomes chronically thickened, and in the middle/late stage, a normal lung tissue structure is destroyed due to overgrowth, alveolar deformation, hardening, and scarring of the lung tissue caused by excessive deposition of extracellular matrix elements such as collagen by fibroblasts, resulting in loss of function.

The fibroblasts play a role in the recruitment of immune cells to sites of inflammation and tissue damage. In addition, the fibroblasts produce and respond to many inflammatory cytokines. Thus, the fibroblasts may contribute to chronic inflammation, and conversely, inflammatory cytokines promote the conversion of fibroblasts to myofibroblasts, thereby promoting fibrosis. Therefore, injury or inflammation of the lung tissue may lead to pulmonary fibrosis.

It has been reported that in the lung tissue of patients with advanced pulmonary fibrosis, TGF-β stimulation induces an increase in ROS production and increased the expression of collagen and α-SMA (a-smooth muscle actin), which are important for fibrosis, and it has been reported that in the lung tissue of patients with idiopathic pulmonary fibrosis, ROS aggravates pulmonary fibrosis.

Therefore, the strains of the present disclosure not only induce antitussive/expectorant action in a cough model mouse, but also inhibit oxidative stress in the chronic respiratory disease animal model to inhibit the expression of inflammatory cytokines, inhibit the expression of MMP-9 to prevent the deposition of immune cells involved in the inflammatory response in the lung tissue and the bronchoalveolar lavage fluid, and inhibit the production of mucous proteins and collagen, thereby ultimately showing an alleviating effect on pulmonary fibrosis.

The present disclosure relates to a pharmaceutical composition for preventing or treating inflammatory diseases or respiratory diseases including the *Lactobacillus plantarum* GCWB1001 strain deposited as accession number KCCM12698P, the *Lactobacillus rhamnosus* GCWB1156 strain deposited as accession number KCCM12700P, or the *Pediococcus acidilactici* GCWB1085 strain deposited as accession number KCCM12699P, one selected from a spray-dried product, a freeze-dried product, a vacuum dried product, a drum dried product, or a crushed product of the strain, or any one of a culture of the strain, and a concentrate, a paste and a dilution of the culture.

The inflammatory diseases may be chronic and acute rhinitis, chronic and acute gastritis, enteritis, ulcerative gastritis, acute and chronic nephritis, acute and chronic hepatitis, chronic obstructive pulmonary disease, pulmonary fibrosis, irritable bowel syndrome, inflammatory bowel disease, enterocolitis, rheumatoid arthritis, osteoarthritis, pneumonia, hepatitis, glomerulonephritis, gastritis, vasculitis, pancreatitis, peritonitis, bronchitis, myocarditis, encephalitis, inflammation in postischemic reperfusion injury, inflammation resulting from immune rejection after transplantation of tissues and organs, burns, psoriasis, various inflammations of the skin, such as allergic contact dermatitis, back pain, myofascial disease, gout, arthritis, rheumatoid arthritis, ankylosing spondylitis, Hodgkin's disease, pancreatitis, conjunctivitis, iritis, scleritis, uveitis, dermatitis, atopic dermatitis, eczema, diabetic inflammation, infectious inflammation caused by a viral or bacterial infection, or autoimmune diseases such as lupus, psoriasis, and atherosclerosis.

The respiratory diseases are caused by any one of fine dust, viral infection, and pneumonia. The respiratory diseases are selected from the group consisting of respiratory inflammatory lung disease, asthma, bronchiectasis, idiopathic pulmonary fibrosis, chronic obstructive pulmonary disease (COPD), cystic fibrosis, emphysema, sequelae of pulmonary tuberculosis, chronic bronchitis, allergic rhinitis, antitussive and expectorant, lower respiratory tract infection, bronchitis, bronchiolitis, acute upper respiratory tract infection, allergic lung disease, bronchiectasis, pneumonia, acute and chronic bronchitis, sinusitis, pharyngitis, tonsillitis, laryngitis and pulmonary fibrosis.

The virus may be selected from adenovirus, vaccinia virus, herpes simplex virus, parainfluenza virus, rhinovirus, varicella Zoster Virus, measle virus, respiratory syncytial virus, Dengue virus, human immunodeficiency virus (HIV), influenza virus, coronavirus, severe acute respiratory syndrome associated virus (SARS-associated virus), and middle east respiratory syndrome coronavirus (MERS-CoV).

The strains of the present disclosure may be used to have a viable cell content of $1\times10^1$ to $1\times10^{13}$ CFU/g, but are not limited thereto.

In addition, the present disclosure relates to a food composition for preventing inflammatory diseases or respiratory diseases including the *Lactobacillus plantarum* GCWB1001 strain deposited as accession number KCCM12698P, the *Lactobacillus rhamnosus* GCWB1156 strain deposited as accession number KCCM12700P, or the *Pediococcus acidilactici* GCWB1085 strain deposited as accession number KCCM12699P, one selected from a spray-dried product, a freeze-dried product, a vacuum dried product, a drum dried product, or a crushed product of the strain, or any one of a culture of the strain, and a concentrate, a paste and a dilution of the culture.

In addition, the present disclosure relates to a health functional food composition for preventing inflammatory diseases or respiratory diseases including the *Lactobacillus plantarum* GCWB1001 strain deposited as accession number KCCM12698P, the *Lactobacillus rhamnosus* GCWB1156 strain deposited as accession number KCCM12700P, or the *Pediococcus acidilactici* GCWB1085 strain deposited as accession number KCCM12699P, one selected from a spray-dried product, a freeze-dried product, a vacuum dried product, a drum dried product, or a crushed product of the strain, or any one of a culture of the strain, and a concentrate, a paste and a dilution of the culture.

In the present disclosure, the food composition or the health functional food composition described above may include ingredients commonly added during food production in addition to the active ingredients, and may include, for example, proteins, carbohydrates, fats, nutrients, seasonings, sweetening agents, and flavoring agents, but are not limited thereto. Examples of the carbohydrates may include monosaccharides, for example, glucose, fructose, and the like; disaccharides, for example, maltose, sucrose, oligosaccharide, and the like; and polysaccharides, for example, general sugars such as dextrin, cyclodextrin, and the like; and sugar alcohols such as xylitol, sorbitol, erythritol, and the like. As the sweetener, natural sweeteners (taumatin, stevia extract, rebaudioside A, glycyrrhizin, etc.) and synthetic sweeteners (saccharin, aspartame, etc.) may be used. In addition, plant-derived oligosaccharides such as fructan, galactan, resistant starch, pectin, beta glucan, and xylo-oligosaccharide, which may be feed of the strain, may be included as probiotics.

However, the present disclosure is not limited thereto, and any ingredient that does not impair the effects of the present disclosure as ingredients known in the art may be used.

Examples of the food composition or the health functional food composition may include patient nutrition food, meat, grains, caffeinated beverages, general drinks, dairy products, chocolate, breads, snacks, confectionery, pizza, jelly, noodles, gums, ice creams, alcoholic beverages, alcohol, vitamin complexes, and other health supplements, but are not limited thereto. When prepared in the form of the food composition or the health functional food composition as described above, it is preferable in that the composition may be easily and conveniently administered.

In the present disclosure, the health functional food composition and the pharmaceutical composition may be prepared in the form of granules, lemonades, powders, syrups, liquids and solutions, extracts, elixirs, fluidextracts, suspensions, decoctions, infusions, tablets, spirits, capsules, troches, pills, and soft or hard gelatin capsules, but are not limited thereto.

The pharmaceutical composition may further include a pharmaceutically acceptable carrier. The pharmaceutically acceptable carrier to be included in the pharmaceutical composition of the present disclosure is generally used in preparation, and includes lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, mineral oil, and the like, but is not limited thereto.

The pharmaceutical composition of the present disclosure may further include a lubricant, a wetting agent, a sweetening agent, a flavoring agent, an emulsifying agent, a suspending agent, a preservative, and the like, in addition to the ingredients.

The pharmaceutical composition of the present disclosure may be administered orally or parenterally.

The pharmaceutical composition of the present disclosure may be formulated by using a pharmaceutically acceptable carrier and/or excipient according to a method that may be easily performed by those skilled in the art to be prepared in a unit dosage form or prepared by introduction into a multi-dosage container.

In addition, the present disclosure relates to probiotics including the *Lactobacillus plantarum* GCWB1001 strain deposited as accession number KCCM12698P, the *Lactobacillus rhamnosus* GCWB1156 strain deposited as accession number KCCM12700P, or the *Pediococcus acidilactici* GCWB1085 strain deposited as accession number KCCM12699P.

The probiotics may include one or more selected from the three types of deposited strains of the present disclosure, may further include one or more selected from the seven types of lactic acid bacteria isolated in the Examples, and may further include known strains useful for the purpose of the present disclosure.

The probiotics may be used with a viable cell content of $1\times10^1$ to $1\times10^{13}$ CFU/g, and the probiotics may be usefully used for preventing or alleviating anti-inflammatory or respiratory diseases.

In the present disclosure, the dosage of the GCWB1001, GCWB1156 and GCWB1085 strains is preferably determined in consideration of the administration method, the age, sex and body weight of a taker, and the severity of the disease.

For example, the GCWB1001, GCWB1156 and GCWB1085 strains may be administered once or separately twice or more at a viable cell content of $1\times10^1$ to $1\times10^{13}$ CFU/g per day.

In addition, the pharmaceutical composition, the food composition, the health functional food composition, and the probiotics including the ingredients may be administered once or separately twice or more at a viable cell content of $1\times10^1$ to $1\times10^{13}$ CFU/g per day based on the active ingredients.

However, the dosage is only an example, and may be changed by a doctor's prescription depending on the user's condition.

Hereinafter, the present disclosure will be described in more detail with reference to the following Examples. However, the following Examples are just illustrative of the present disclosure and the scope of the present disclosure is not limited thereto.

MODE FOR INVENTION

Example 1: Isolation and Identification of *Lactobacillus plantarum* GCWB1001 Strain (1) Isolation of Strain Kimchi collected from each local region was put in the sterilized physiological saline of an amount equal to 10 times the Kimchi and homogenized. The homogenized sample was diluted in sterilized physiological saline by 10 steps, and the strain was isolated by a dilution plating method. The diluted strain sample was smeared on an MRS medium (MRS broth agar; BD Difco) and then anaerobically cultured at 37° C. for 72 hours. Colonies appearing on the MRS agar plate were inoculated secondly in a PCA medium (MBcell, South Korea) containing 0.005% bromocresol purple (BCP) as a pH indicator, and colonies in which the purple medium turned to yellow were thirdly inoculated on the MRS agar plate to purely isolate probiotics.

(2) Identification of *Lactobacillus plantarum* GCWB1001 Strain

DNA extraction and purification were performed on the strain purely isolated in (1) above. After 16s rRNA gene amplification was performed using two universal primers, 27F (5'-AGAGTTTGATCMTGGCTCAG-3') (SEQ ID NO: 4) and 1492R (5'-TACGGYTACCTTGTTACGACTT-3') (SEQ ID NO: 5), sequencing analysis of the amplified 16s rRNA gene was performed. Only two types of strains corresponding to Generally Recognized as Safe (GRAS) were selected using the analyzed 16s rRNA sequence data and EzTaxon server (ezbiocloud.net), and shown in Table 1 below.

TABLE 1

| Identified strain |
|---|
| *Lactobacillus plantarum* GCWB1001 |
| *Leuconostoc mesenteroides* GCWB1031 |

The 16S rRNA sequencing results of the *Lactobacillus plantarum* GCWB1001 are as follows.

```
<16S rRNA sequence of Lactobacillus plantarum
GCWB1001>
GGTCGTACGA ACTCTGTGTA TTGATTGGTG CTTGCATCAT

GATTTACATT TGCAGTGAGT
```

-continued

```
GGCGAACTGG TGAGTAACAC GTGGGAAACC TGCCCAGAAG

CGGGGGATAA CACCTGGAAA

CAGATGCTAA TACGGCATAA CAACTTGGAC CGCATGGTCC

GAGTTTGAAA GATGGCTTCG

GCTATCACTT TTGGATGGTC CCGCGGCGTA TTAGCTAGAT

GGTGGGGTAA CGGCTCACCA

TGGCAATGAT ACGTAGCCGA CCTGAGAGGG TAATCGGCCA

CATTGGGACT GAGACACGGC

CCAAACTCCT ACGGGAGGCA GCAGTAGGGA ATCTTCCACA

ATGGACGAAA GTCTGATGGA

GCAACGCCGC GTGAGTGAAG AAGGGTTTCG GCTCGTAAAA

CTCTGTTGTT GAAGAAGAAC

ATATCTGAGA GTAACTGTTC AGGTATTGAC GGTATTTAAC

CAGAAAGCCA CGGCTAACTA

CGTGCCAGCA GCCGCGGTAA TACGTAGGTG GCAAGCGTTG

TCCGGATTTA TTGGGCGTAA

AGCGAGCGCA GGCGGTTTTT TAAGTCTGAT GTGAAAGCCT

TCGGCTCAAC CGAAGAAGTG

CATCGGAAAC TGGGAAACTT GAGTGCAGAA GAGGACAGTG

GAACTCCATG TGTAGCGGTG

AAATGCGTAG ATATATGGAA GAACACCAGT GGCGAAGGCG

GCTGTCTGGT CTGTAACTGA

CGCTGAGGCT CGAAAGTATG GGTAGCAAAC AGGATTAGAT

ACCCTGGTAG TCCATACCGT

AAACGATGAA TGCTAAGTGT TGGAGGGTTT CCGCCCTTCA

GTGCTGCAGC TAACGCATTA

AGCATTCCGC CTGGGGAGTA CGGCCGCAAG GCTGAAACTC

AAAGGAATTG ACGGGGGCCC

GCACAAGCGG TGGAGCATGT GGTTTAATTC GAAGCTACGC

GAAGAACCTT ACCAGGTCTT

GACATACTAT GCAAATCTAA GAGATTAGAC GTTCCCTTCG

GGGACATGGA TACAGGTGGT

GCATGGTTGT CGTCAGCTCG TGTCGTGAGA TGTTGGGTTA

AGTCCCGCAA CGAGCGCAAC

CCTTATTATC AGTTGCCAGC ATTAAGTTGG GCACTCTGGT

GAGACTGCCG GTGACAAACC

GGAGGAAGGT GGGGATGACG TCAAATCATC ATGCCCCTTA

TGACCTGGGC TACACAGGTG

CTACAATGGA TGGTACAACG AGTTGCGAAC TCGCGAGAGT

AAGCTAATCT CTTAAAGCCA
```

-continued

```
TTCTCAGTTC GGATTGTAGG CTGCAACTCG CCTACATGAA

GTCGGAATCG CTAGTAATCG

CGGATCAGCA TGCCGCGGTG AATACGTTCC CGGGCCTTGT

ACACACCGCC CGTCACACCA

TGAGAGTTTG TAACACCCAA AGTCGGTGGG GTAACCTTTT

AGGAACCAGC CGCT
```

Example 2: Isolation and Identification of *Pediococcus acidilactici* GCWB1085 Strain (1) Isolation of Strain Cheese collected from each local region was put in sterilized physiological saline of an amount equal to 10 times the Kimchi and homogenized. The homogenized sample was diluted in sterilized physiological saline by 10 steps, and the strain was isolated by a dilution plating method. The diluted strain sample was smeared on an MRS medium (MRS broth agar; BD Difco) and then anaerobically cultured at 37° C. for 72 hours. Colonies appearing on the MRS agar plate were inoculated secondly in a PCA medium (MBcell, South Korea) containing 0.005% bromocresol purple (BCP) as a pH indicator, and colonies in which the purple medium turned to yellow were thirdly inoculated on the MRS agar plate to purely isolate probiotics.

(2) Identification of *Pediococcus acidilactici* GCWB1085 Strain

Chromosomal DNA extraction and purification were performed on the strain purely isolated in (1) above. After 16s rRNA gene amplification was performed using two universal primers, 27F (5'-AGAGTTTGATCMTGGCTCAG-3') (SEQ ID NO: 4) and 1492R (5'-TACGGYTACCTTGT-TACGACTT-3') (SEQ ID NO: 5), sequencing analysis of the amplified 16s rRNA gene was performed. Only four types of strains corresponding to Generally Recognized as Safe (GRAS) were selected using the analyzed 16s rRNA sequence data and EzTaxon server (ezbiocloud.net), and shown in Table 2 below.

TABLE 2

| Identified strain |
| --- |
| *Pediococcus acidilactici* GCWB1085 |
| *Lactobacillus paracasei* GCWB1084 |
| *Bifidobacterium longum* GCWB1136 |

The 16S rRNA sequencing results of the *Pediococcus acidilactici* GCWB1085 are as follows.

```
<16S rRNA sequence of Pediococcus acidilactici
GCWB1085>
CTCAGGATGA ACGCTGGCGG CGTGCCTAAT ACATGCAAGT

CGAACGAACT TCCGTTAATT

GATCAGGACG TGCTTGCACT GAATGAGATT TTAACACGAA

GTGAGTGGCG GACGGGTGAG

TAACACGTGG GTAACCTGCC CAGAAGCAGG GGATAACACC

TGGAAACAGA TGCTAATACC
```

-continued

```
GTATAACAGA GAAAACCGCC TGGTTTTCTT TTAAAAGATG

GCTCTGCTAT CACTTCTGGA

TGGACCCGCG GCGCATTAGC TAGTTGGTGA GGTAACGGCT

CACCAAGGCG ATGATGCGTA

GCCGACCTGA GAGGGTAATC GGCCACATTG GGACTGAGAC

ACGGCCCAGA CTCCTACGGG

AGGCAGCAGT AGGGAATCTT CCACAATGGA CGCAAGTCTG

ATGGAGCAAC GCCGCGTGAG

TGAAGAAGGG TTTCGGCTCG TAAAGCTCTG TTGTTAAAGA

AGAACGTGGG TGAGAGTAAC

TGTTCACCCA GTGACGGTAT TTAACCAGAA AGCCACGGCT

AACTACGTGC CAGCAGCCGC

GGTAATACGT AGGTGGCAAG CGTTATCCGG ATTTATTGGG

CGTAAAGCGA GCGCAGGCGG

TCTTTTAAGT CTAATGTGAA AGCCTTCGGC TCAACCGAAG

AAGTGCATTG GAAACTGGGA

GACTTGAGTG CAGAAGAGGA CAGTGGAACT CCATGTGTAG

CGGTGAAATG CGTAGATATA

TGGAAGAACA CCAGTGGCGA AGGCGGCTGT CTGGTCTGTA

ACTGACGCTG AGGCTCGAAA

GCATGGGTAG CGAACAGGAT TAGATACCCT GGTAGTCCAT

GCCGTAAACG ATGATTACTA

AGTGTTGGAG GGTTTCCGCC CTTCAGTGCT GCAGCTAACG

CATTAAGTAA TCCGCCTGGG

GAGTACGACC GCAAGGTTGA AACTCAAAG AATTGACGGG

GGCCCGCACA AGCGGTGGAG

CATGTGGTTT AATTCGAAGC TACGCGAAGA ACCTTACGAG

GTCTTGACAT CTTCTGCCAA

CCTAAGAGAT TAGGCGTTCC CTTCGGGGAC AGAATGACAG

GTGGTGCATG GTTGTCGTCA

GCTCGTGTCG TGAGATGTTG GGTTAAGTCC CGCAACGAGC

GCAACCCTTA TTACTAGTTG

CCAGCATTGA GTTGGGCACT CTAGTGAGAC TGCCGGTGAC

AAACCGGAGG AAGGTGGGGA

CGACGTCAAA TCATCATGCC CCTTATGACC TGGGCTACAC

ACGTGCTACA ATGGATGGTA

CAACGAGTTG CGAAACCGCG AGGTTTAGCT AATCTCTTAA

AACCATTCTC AGTTCGGACT

GTAGGCTGCA ACTCGCCTAC ACGAAGTCGG AATCGCTAGT

AATCGCGGAT CAGCATGCCG

CGGTGAATAC GTTCCCGGGC CTTGTACACA CCGCCCGTCA
```

-continued

CACCATGAGA GTTTGTAACA

CCCAAAGCCG GTGGGGTAAC CTTTTAGGAG CTAGCCGTCT

AAGGTGGGAC AGATGATTA

Example 3: Isolation and Identification of
*Lactobacillus rhamnosus* GCWB1156 Strain (1) Isolation of Strain The feces of healthy infants born through natural delivery were diluted in sterilized physiological saline by 10 steps, and the strain was isolated by a dilution plating method. The diluted fecal sample was smeared on a BSM agar medium (*Bifidus* Selective Medium Agar; Sigma, USA) and then anaerobically cultured at 37° C. for 72 hours. Colonies appearing on the BSM agar plate were inoculated secondly in a PCA medium (MBcell, South Korea) containing 0.005% bromocresol purple (BCP) as a pH indicator, and colonies in which the purple medium turned to yellow were thirdly inoculated on a BL agar medium (MBcell, South Korea) to purely isolate probiotics.

(2) Identification of *Lactobacillus rhamnosus* GCWB1156 Strain

Chromosomal DNA extraction and purification were performed on the strain purely isolated in (1) above. After 16s rRNA gene amplification was performed using two universal primers, 27F (5'-AGAGTTTGATCMTGGCTCAG-3') (SEQ ID NO: 4) and 1492R (5'-TACGGYTACCTTGT-TACGACTT-3') (SEQ ID NO: 5), sequencing analysis of the amplified 16s rRNA gene was performed. Only one type of strain corresponding to Generally Recognized as Safe (GRAS) was selected using the analyzed 16s rRNA sequence data and EzTaxon server (ezbiocloud.net) and shown in Table 3 below.

TABLE 3

| Identified strain |
| --- |
| *Lactobacillus rhamnosus* GCW1156 |
| *Bifidobacterium breve* GCWB1144 |

The 16S rRNA sequencing results of the *Lactobacillus rhamnosus* GCWB1156 are as follows.

<16S rRNA sequence of *Lactobacillus rhamnosus*
GCW1156>
GTTGATCGGC CACATTGGGA CTGAGACACG GCCCAAACTC

CTACGGGAGG CAGCAGTAGG

GAATCTTCCA CAATGGACGC AAGTCTGATG GAGCAACGCC

GCGTGAGTGA AGAAGGCTTT

CGGGTCGTAA AACTCTGTTG TTGGAGAAGA ATGGTCGGCA

GAGTAACTGT TGTCGGCGTG

ACGGTATCCA ACCAGAAAGC CACGGCTAAC TACGTGCCAG

CAGCCGCGGT AATACGTAGG

TGGCAAGCGT TATCCGGATT TATTGGGCGT AAAGCGAGCG

CAGGCGGTTT TTTAAGTCTG

-continued
ATGTGAAAGC CCTCGGCTTA ACCGAGGAAG TGCATCGGAA

ACTGGGAAAC TTGAGTGCAG

AAGAGGACAG TGGAACTCCA TGTGTAGCGG TGAAATGCGT

AGATATATGG AAGAACACCA

GTGGCGAAGG CGGCTGTCTG GTCTGTAACT GACGCTGAGG

CTCGAAAGCA TGGGTAGCGA

ACAGGATTAG ATACCCTGGT AGTCCATGCC GTAAACGATG

AATGCTAGGT GTTGGAGGGT

TTCCGCCCTT CAGTGCCGCA GCTAAGGCAT TAAGCATTCC

GCCTGGGGAG TACGACCGCA

AGGTTGAAAC TCAAAGGAAT TGACGGGGGC CCGCACAAGC

GGTGGAGCAT GTGGTTTAAT

TCGAAGCAAC GCGAAGAACC TTACCAGGTC TTGACATCTT

TTGATCACCT GAGAGATCAG

GTTTCCCCTT CGGGGGCAAA ATGACAGGTG GTGCATGGTT

GTCGTCAGCT CGTGTCGTGA

GATGTTGGGT TAAGTCCCGC AACGAGCGCA ACCCTTATGA

CTAGTTGCCA GCATTTAGTT

GGGCACTCTA GTAAGACTGC CGGTGACAAA CCGGAGGAAG

GTGGGGATGA CGTCAAATCA

TCATGCCCCT TATGACCTGG GCTACACACG TGCTACAATG

GATGGTACAA CGAGTTGCGA

GACCGCGAGG TCAAGCTAAT CTCTTAAAGC CATTCTCAGT

TCGGACTGTA GGCTGCAACT

CGCCTACACG AAGTCGGAAT CGCTAGTAAT CGCGGATCAG

CACGCCGCGG TGAATACGTT

CCCGGGCCTT GTACACACCG CCCGTCACAC CATGAGAGTT

TGTAACACCC GAAGCCGGTG

GCGTAACCCT TTTAGGGAGC GAGCCGTCTA AGGTGGGACA

AATGATTA

Experiment Example 1: Analysis of
Anti-Inflammatory Effect in Mouse Lung
Macrophages 1-1) Evaluation of Cytotoxicity of Strains (LDH Leakage and CCK-8 Assay)

A mouse alveolar macrophage cell line, MH-S cell line was received from the American Type Culture Collection (ATCC, Manassas, VA, USA), suspended so that the cell concentration was $5 \times 10^5$ cells/ml, dispensed by 100 µl into a 96-well plate, treated with each sample for each concentration, and then cultured for 48 hours. The cytotoxicity was measured using an MTT assay kit and a Cytotoxicity LDH Assay Kit, and the results are shown in Table 4 below.

TABLE 4

| Classification | Dose (µg/ml) | LDH (fold of control) (24 hr) | MTT (% of control) (24 hr) |
|---|---|---|---|
| Normal group (No treatment) | 0 | 1.00 ± 0.04 | 100.0 ± 2.12 |
| Excipient (100% maltodextrin) | 1000 | 0.99 ± 0.02 | 99.6 ± 3.13 |
| Lactobacillus plantarum | 10 | 0.99 ± 0.03 | 101.7 ± 3.4 |
| | 100 | 1.01 ± 0.03 | 102.3 ± 4.17 |
| GCWB1001 | 1000 | 0.60 ± 0.02* | 101.5 ± 3.2 |
| GCWB1031 | 10 | 1.00 ± 0.02 | 104.8 ± 8.9 |
| | 100 | 1.03 ± 0.06 | 100.9 ± 2.88 |
| | 1000 | 0.85 ± 0.02* | 98.2 ± 3.8 |
| GCWB1084 | | 1.01 ± 0.03 | 96.4 ± 1.94 |
| | 100 | 1.18 ± 0.26 | 100.0 ± 1.57 |
| | 1000 | 1.20 ± 0.03 | 93.4 ± 0.4 |
| Pediococcus acidilactici | 10 | 0.98 ± 0.02 | 108.95 ± 5.31 |
| | 100 | 0.95 ± 0.03 | 113.06 ± 4.63** |
| GCWB1085 | 1000 | 0.58 ± 0.03* | 102.03 ± 1.39 |
| Lactobacillus rhamnosus | 10 | 0.87 ± 0.03 | 99.9 ± 1.26 |
| | 100 | 0.82 ± 0.02* | 98.3 ± 0.63 |
| GCWB1156 | 1000 | 0.90 ± 0.01 | 93.5 ± 4.8 |
| GCWB1136 | 10 | 1.01 ± 0.00 | 101.4 ± 3.08 |
| | 100 | 0.87 ± 0.02 | 99.1 ± 3.14 |
| | 1000 | 0.81 ± 0.02* | 97.1 ± 3.92 |
| GCWB1144 | 10 | 0.87 ± 0.04 | 102.3 ± 4.03 |
| | 100 | 0.82 ± 0.02** | 96.4 ± 1.56 |
| | 1000 | 0.79 ± 0.02* | 95.7 ± 2.88 |

*P < 0.001 vs. normal group.

**P < 0.01 vs. normal group.

(1) LDH Assay Result 7 types of lactic acid bacteria of Table 3 above were treated in mouse MH-S lung macrophages at a concentration of 1 to 1,000 µg/ml for 24 hours and then LDH assay was performed, and as a result, cytotoxicity was not observed for all of the 7 types. However, it was confirmed that the LDH values were significantly reduced at the concentration of 1,000 µg/ml of the GCWB1001, GCWB1085, GCWB1176, and GCWB1156 strains, and thus all of the strains had no cytotoxicity.

(2) MTT Assay Result 7 types of lactic acid bacteria of Table 4 above were treated in mouse MH-S lung macrophages at a concentration of 1 to 1,000 µg/ml for 24 hours and then MTT assay was performed, and as a result, cytotoxicity was not observed at the concentration of 100 µg/ml or less for all of the 7 types. However, cytotoxicity was confirmed at a concentration of 100 µg/ml of the GCWB1085 strain.

1-2) Measurement of Cytokine Secretion (TNF-Alpha, TGF-Beta)

An MH-S cell line was pretreated with a sample for 1 hour and then treated with LPS (10 ng/ml) or ConA (10 µg/ml) and DEP (200 µg/ml) for 3 hours and 26 hours, respectively, and the amounts of cytokines (TNF-alpha and TGF-beta) secreted into a culture medium were measured using an ELISA kit (R&D system, USA), and the results are shown in Table 5 and FIG. 1 below.

TABLE 5

| Classification | Dose (µg/ml) | TNF-alpha inhibition rate (%) |
|---|---|---|
| Normal group (No treatment) | — | 52.4 |
| Control group (LPS10 ng/ml + DEP 20 0 µg/ml) | — | 100 ## |
| LPS10 ng/ml + DEP 20 0 µg/ml | *Lactobacillus plantarum* 10 | 58.1* |
| | 100 | 74.2* |

TABLE 5-continued

| Classification | Dose (µg/ml) | TNF-alpha inhibition rate (%) |
|---|---|---|
| GCWB1001 | 1000 | 89.7** |
| GCWB1031 | 10 | 86.8** |
| | 100 | 130.0 |
| | 1000 | 157.4 |
| *Pediococcus acidilactici* | 10 | 90.2*** |
| | 100 | 60.0* |
| GCWB1085 | 1000 | 54.8* |
| *Lactobacillus rhamnosus* | 10 | 66.7* |
| | 100 | 66.9** |
| GCWB1156 | 1000 | 105.6 |
| GCWB1136 | 10 | 304.7 |
| | 100 | 370.4 |
| | 1000 | 1270.8 |
| GCWB1144 | 10 | 449.1 |
| | 100 | 1573.7 |
| | 1000 | 3401.6 |

P < 0.01 vs. normal group.

*P < 0.001 vs LPS 10 ng/ml + DEP 200 µg/ml,

**P < 0.01 vs. LPS 10 ng/ml + DEP 200 µg/ml.

***P < 0.05 vs. LPS 10 ng/ml + DEP 200 µg/ml.

(1) TNF-Alpha Measurement Result

As shown in Table 5, cytokine TNF-alpha secretion by LPS and DEP treatment in MH-S cells was decreased at most of treatment concentrations in all of the strains of GCWB1001, GCWB1084 and GCWB1156. Therefore, the strains of the present disclosure reduced the secretion of TNF-alpha, which is a proinflammatory cytokine caused by fine dust, in a concentration-dependent manner.

(2) TGF-β Measurement Result

As shown in FIG. 1, the secretion of TGF-beta caused by fine dust was decreased when 1 µg/ml and 10 µg/ml of GCWB1001, GCWB1085 and GCWB1156 strains were treated.

1-3) Measurement of Nitric Oxide (NO)

A mouse lung macrophage line, NH—S cell line was suspended so that the cell concentration was $5 \times 10^5$ cells/ml, and dispensed into a 96-well plate by 100 µl. 7 types of strains of Table 6 as samples were pretreated for 1 hour at concentrations of 1 µg/ml and 10 µg/ml, respectively, and then treated with LPS 100 ng/ml for 24 hours. Then, 50 µl of the culture solution was transferred to a 96-well plate, mixed with Griess reagent I (NED solution) and Griess reagent II (Sulfanilamide solution) in equal amounts, reacted in a dark room for 10 minutes, and then measured at 540 nm using a microplate reader within 30 minutes.

TABLE 6

| Classification | | Dose (µg/ml) | NO (µM) |
|---|---|---|---|
| Normal group (No Treatment) | — | — | 0.42 ± 0.00 |
| Control group (LPS 10 ng/ml + DEP 200 µg/ml ) | — | — | 4.88 ± 0.32# |
| LPS 10 ng/ml + DEP 200 µg/ml | *Lactobacillus plantarum* GCWB1001 | 1 | 4.26 ± 0.44 |
| | | 10 | 4.47 ± 0.60 |
| | GCWB1031 | 1 | 3.91 ± 0.24** |
| | | 10 | 5.16 ± 0.74 |
| | GCWB1084 | 1 | 2.90 ± 0.36* |
| | | 10 | 8.30 ± 0.12* |
| | *Pediococcus acidilactici* GCWB1085 | 1 | 3.20 ± 0.32* |
| | | 10 | 5.51 ± 1.058 |
| | *Lactobacillus* GCWB1156 | 1 | 4.19 ± 0.21*** |

TABLE 6-continued

| Classification | Dose (μg/ml) | NO (μM) |
|---|---|---|
| rhamnosus | 10 | 4.47 ± 0.12 |
| GCWB1136 | 1 | 5.37 ± 0.99 |
| | 10 | 7.74 ± 0.21 |
| GCWB1144 | 1 | 5.09 ± 0.48 |
| | 10 | 8.44 ± 0.53* |

P < 0.001 vs. normal group.
*P < 0.001 vs. LPS 10 ng/ml + DEP 200 μg/ml treated group.
**P < 0.01 vs. LPS 10 ng/ml + DEP 200 μg/ml treated group.
***P < 0.05 vs. LPS 10 ng/ml + DEP 200 μg/ml treated group.

Figure 2:
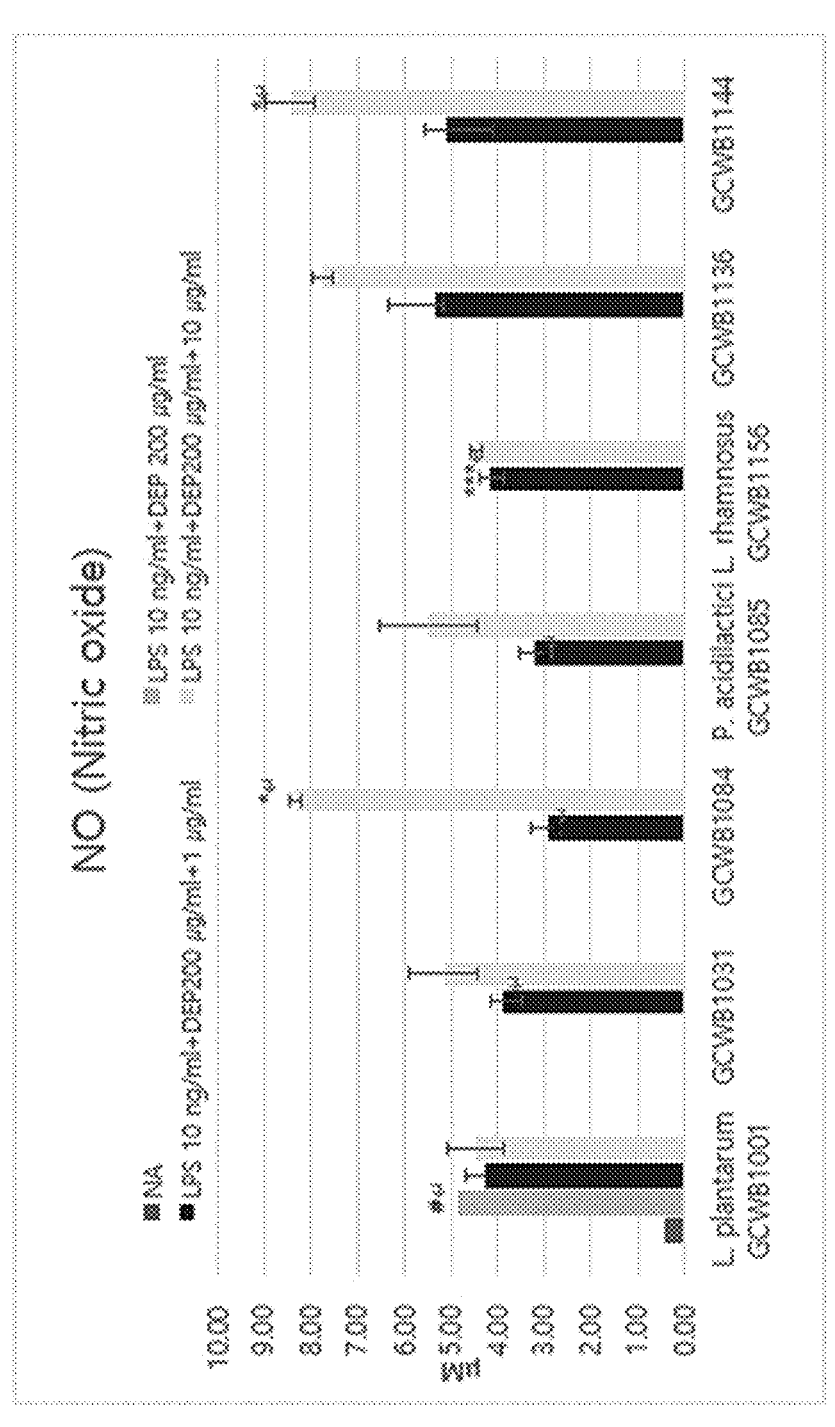
FIGS. 2 and 3 are graphs showing the measurement of the NO and ROS production amount by 7 types of strain samples in a mouse lung macrophage cell line (MH-S) (Experimental Examples 1-3 and 1-4).

The experimental results are shown graphically in FIG. 2. As can be seen from Table 6 and FIG. 2, it was confirmed that all of the GCWB1001, GCWB1085 and GCWB1156 strains of the present disclosure significantly reduced the NO production amount by fine dust at a concentration of 1 μg/ml. However, the strains did not significantly reduce the NO production amount by fine dust at a concentration of 10 μg/ml.

1-4) Measurement of Reactive Oxygen Species (ROS)

A mouse lung macrophage line, NH—S cell line was suspended so that the cell concentration was $5 \times 10^5$ cells/ml, and dispensed into a 96-well plate by 100 μl. 7 types of strains of Table 6 above as samples were pre-treated for 1 hour at a concentration of 1 μg/ml and 10 μg/ml, respectively, and then treated with LPS 100 ng/ml for 6 hours, and washed with HBSS, and the culture solution was treated with DCF-DA (2',7'-Dichlorofluorescein diacetate)/HBSS at 25 μM per well for 30 minutes, and then fluorescence values were measured at an excitation wavelength of 485 nm and an emission wavelength of 530 nm.

Figure 3:
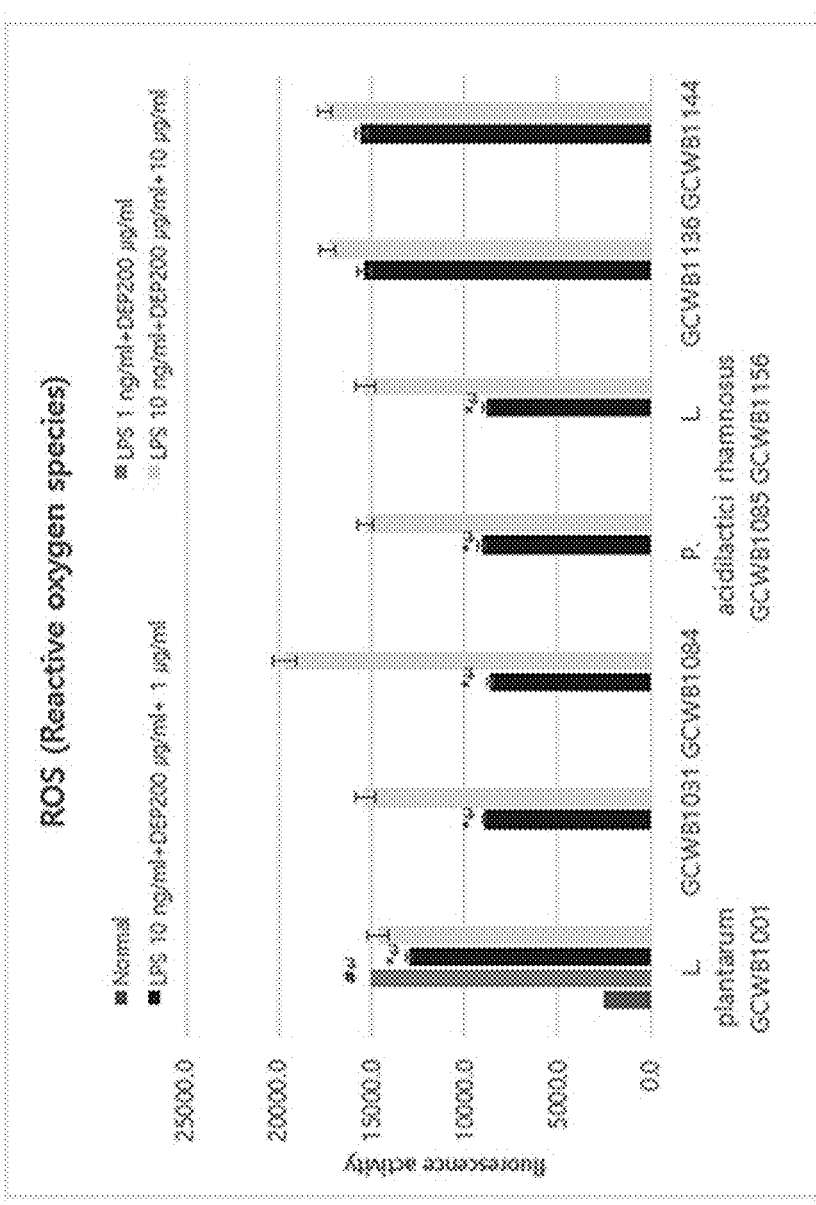

The experimental results are shown graphically in FIG. 3. It was confirmed that the GCWB1001, GCWB1085 and GCWB1156 strains of the present disclosure all significantly reduced the production amount of ROS caused by fine dust at a concentration of 1 μg/ml, similarly to the NO analysis.

1-5) Measurement of Inflammatory Transcriptional Regulator Activity (iNOS-Luc, COX2-Luc, NF-kB-Luc; Luciferase Promoter Activity Analysis)

After MH-S cells were dispensed at $1 \times 10^6$ cells/ml, plasmid vectors into which iNOS-Luc, COX2-Luc, and NF-kB-Luc were inserted were introduced into the cells using a LIPOFECTAMINE™ 2000 reagent (Invitrogen, Carlsbad, CA). After the samples were treated for 24 hours by concentration, the cells were collected and the luciferase activity was measured.

Figure 4:
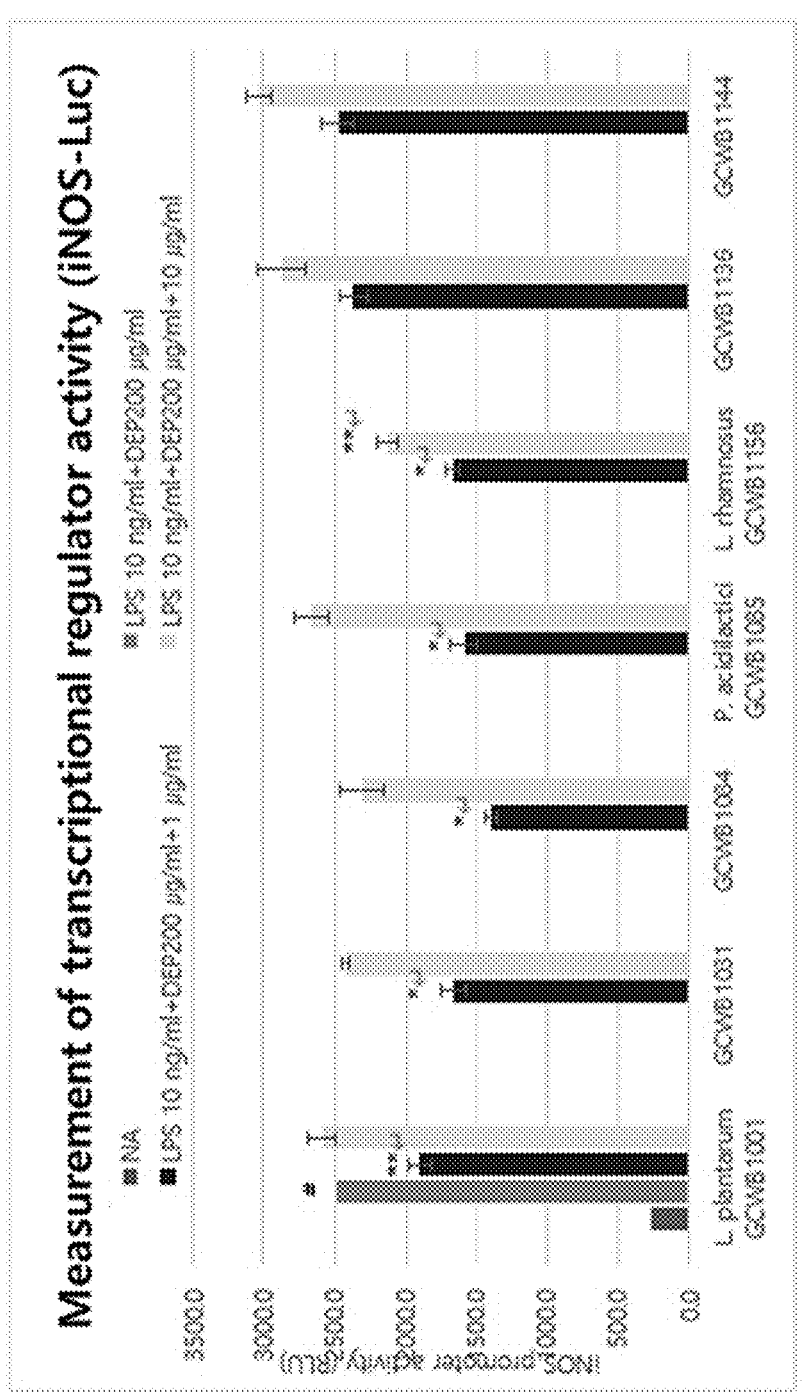
FIGS. 4 to 6 are graphs showing the measurement of the inflammatory transcriptional regulator activities (promoter activities of iNOS, COX2 and NF-kB) by 7 types of strain samples in a mouse lung macrophage cell line (MH-S) (Experimental Example 1-5).
Figure 5:
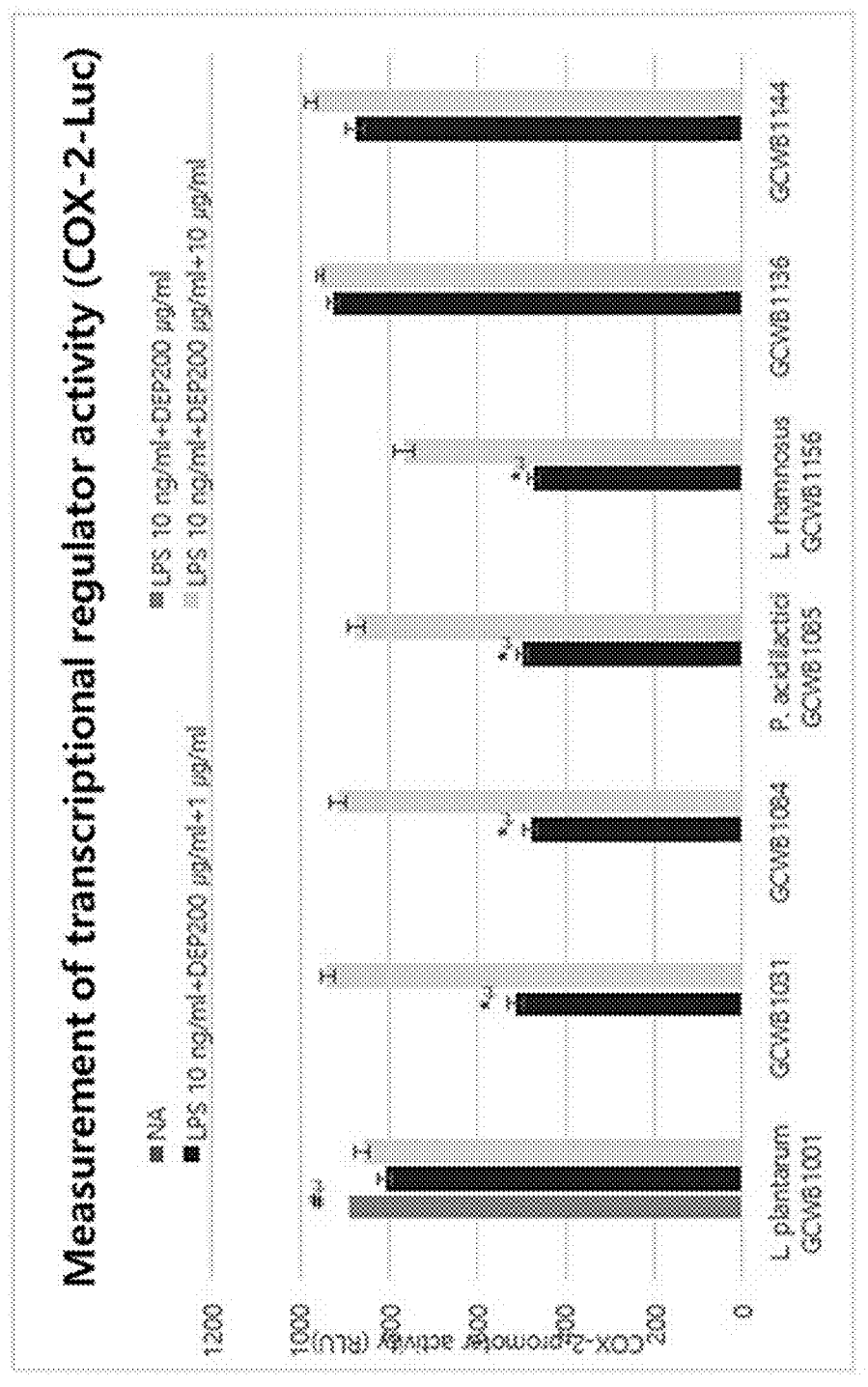
Figure 6:
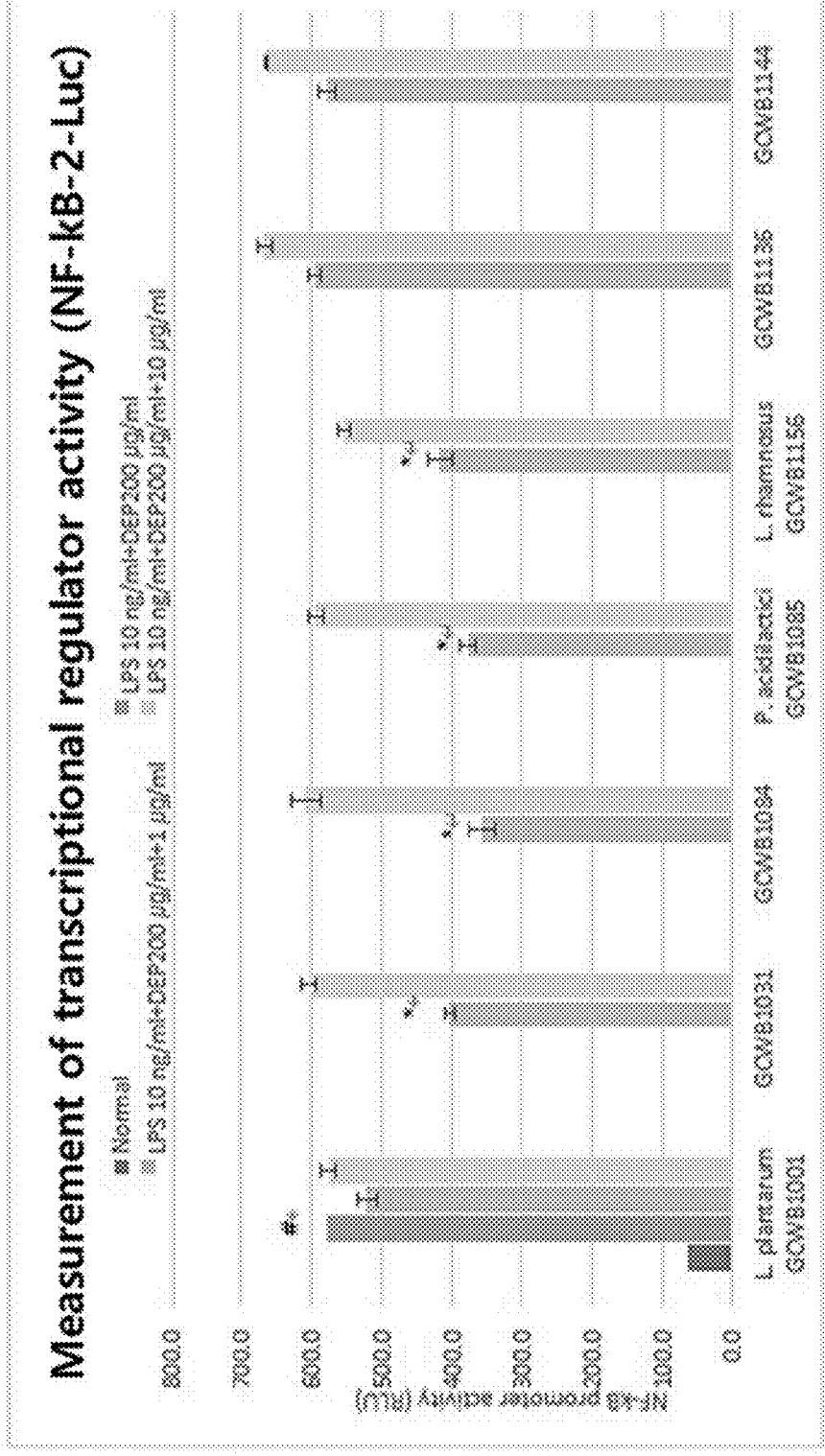

According to FIGS. 4 to 6, the promoter activities of iNOS, COX2, and NF-kB, which are inflammatory transcription factors caused by fine dust, were reduced when the GCWB1001, 1085, and 1156 strains were treated at 1 μg/ml. Overall, the strains of the present disclosure may inhibit the expression inflammation-related genes by inhibiting the promoter activities of an NF-kB transcription factor inhibiting the expression of inflammation-related genes and iNOS and COX genes known as inflammatory genes.

Experiment Example 2: Study on Antitussive/Expectorant Effect in Animal Model (In Vivo Assay)

2-1) Experimental Conditions and Breeding Conditions

Experimental animals were supplied with 6-week-old male BALB/c mice (body weight: 20±2 g) from Samtako Co., Ltd., and acclimatized for 7 days or more in an animal breeding room at a temperature of 23±1° C., relative humidity of 55±15%, and illuminance of 300 to 500 Lux with brightness adjusted at intervals of 12 hours. Thereafter, only normal animals were used for the experiment by observing the visual symptoms, and solid feed for laboratory animals (Samtako Co., Ltd.) and water were freely fed. All animal experiments were performed with the approval of the Laboratory Animal Ethics Committee of Korea International University, and performed according to the guidelines of the US National Institutes of Health (NIH publication No. 86-23, revised 1985).

2-2) Study on Antitussive Effect

Experimental groups consisted of 4 groups: 1 M citric acid alone administered group (control), citric acid+Synatura 200 mg/kg (positive control), citric acid+sample treated group ($1 \times 10^7$), and citric acid+sample treated group ($1 \times 10^9$), and the number of animals per experimental group was 8 (n=8) (Table 7).

TABLE 7

| No | Experimental group (n = 8) | Concentration |
|---|---|---|
| 1 | Citric acid (control) | 1 M |
| 2 | Citric acid + Synatura | 200 mg/kg |
| 3 | Citric acid + sample treated group | $1 \times 10^7$ cfu |
| 4 | Citric acid + sample treated group | $1 \times 10^9$ cfu |

Figure 7:
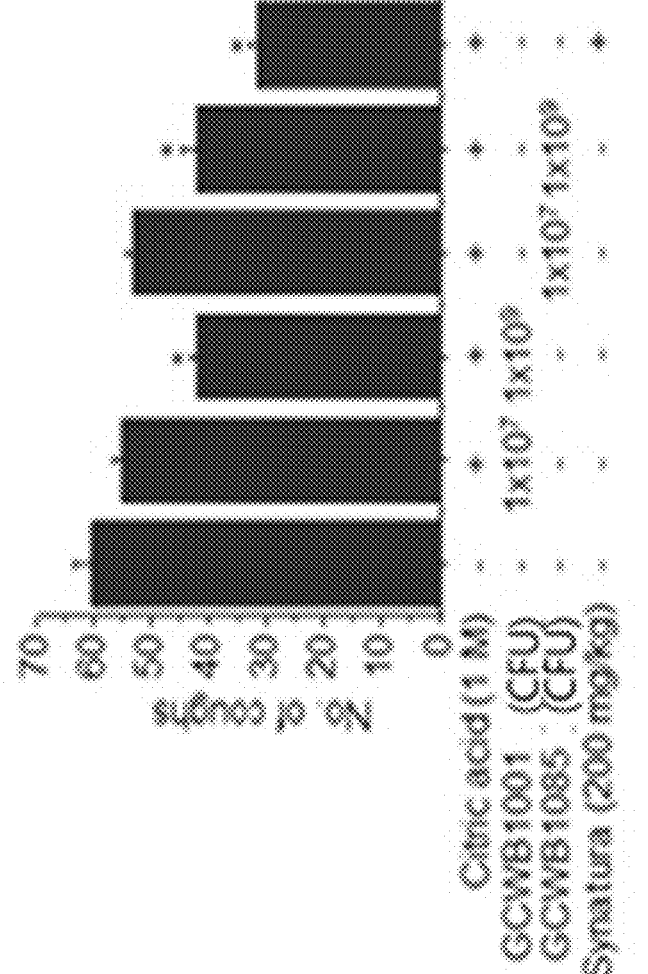
FIGS. 7 and 8 are graphs showing the antitussive and expectorant actions of GCWB1001, GCWB1085 and GCWB1156 strains in a mouse cough model (Experimental Examples 2-2 and 2-3).

After oral administration of the sample for 1 hour, 1 M citric acid, which is a cough inducer, was intranasally administered, and then respective experimental groups were placed in a chamber, and the number of coughs was measured for 10 minutes. As a result, as shown in FIG. 7, both GCWB1001 and GCWB1085 strains significantly reduced the number of coughs caused by citric acid after administration of $1 \times 10^9$ cfu.

2-3) Study on Expectorant Effect

Experimental groups consisted of 4 groups: 1 M phenol-red administered group (control), phenol-red+Synatura 200 mg/kg (positive control), phenol-red+sample treated group ($1 \times 10^7$), and phenol-red+sample treated group ($1 \times 10^9$), and the number of animals per experimental group was 8 (n=8) (Table 8).

TABLE 8

| No | Experimental group | Concentration |
|---|---|---|
| 1 | Phenol red + Saline | 10 mg/kg |
| 2 | Phenol red + Synatura | 200 mg/kg |
| 3 | Phenol red + sample treated group | $1 \times 10^7$ cfu |
| 4 | Phenol red + sample treated group | $1 \times 10^9$ cfu |

After oral administration of the samples, 0.2 ml of phenol red (10 mg/ml) was intraperitoneally injected after 1 hour, the experimental animals were sacrificed after 30 minutes, and then the trachea was extracted.

After measuring the weight of the extracted organ, 0.5 ml of 0.9% Saline (w/v) was added and vortexed. After 100 μl of 1 M NaOH as a color development substrate was added, the absorbance at 550 nm was measured.

Figure 8:
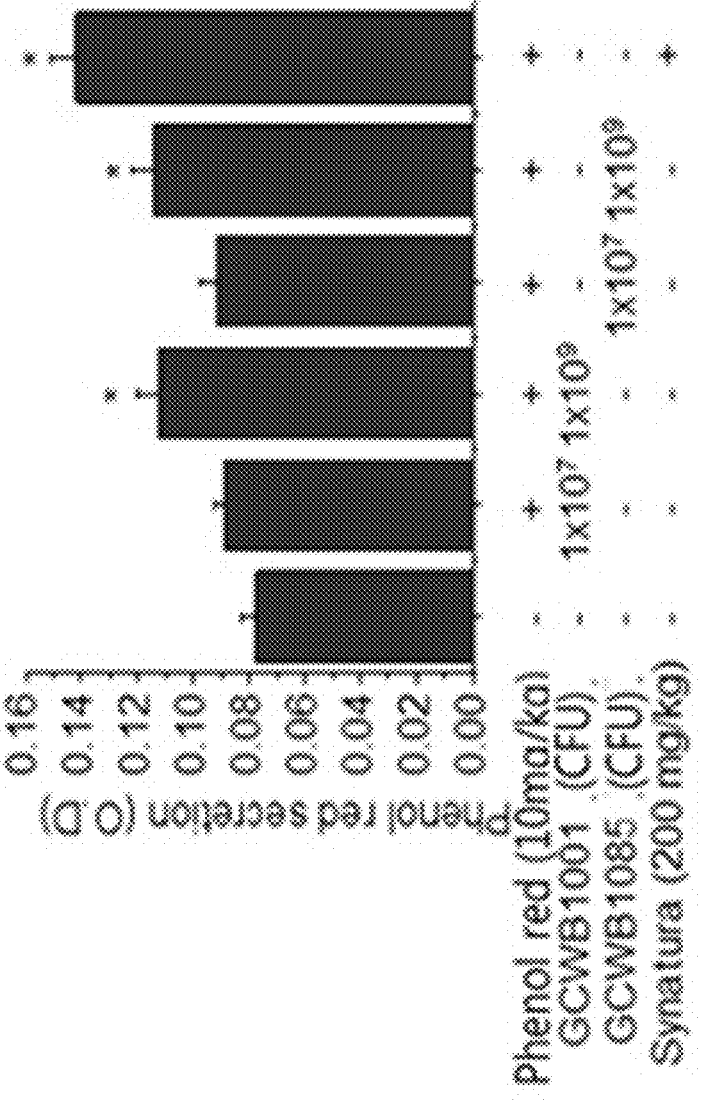
Figure 9:
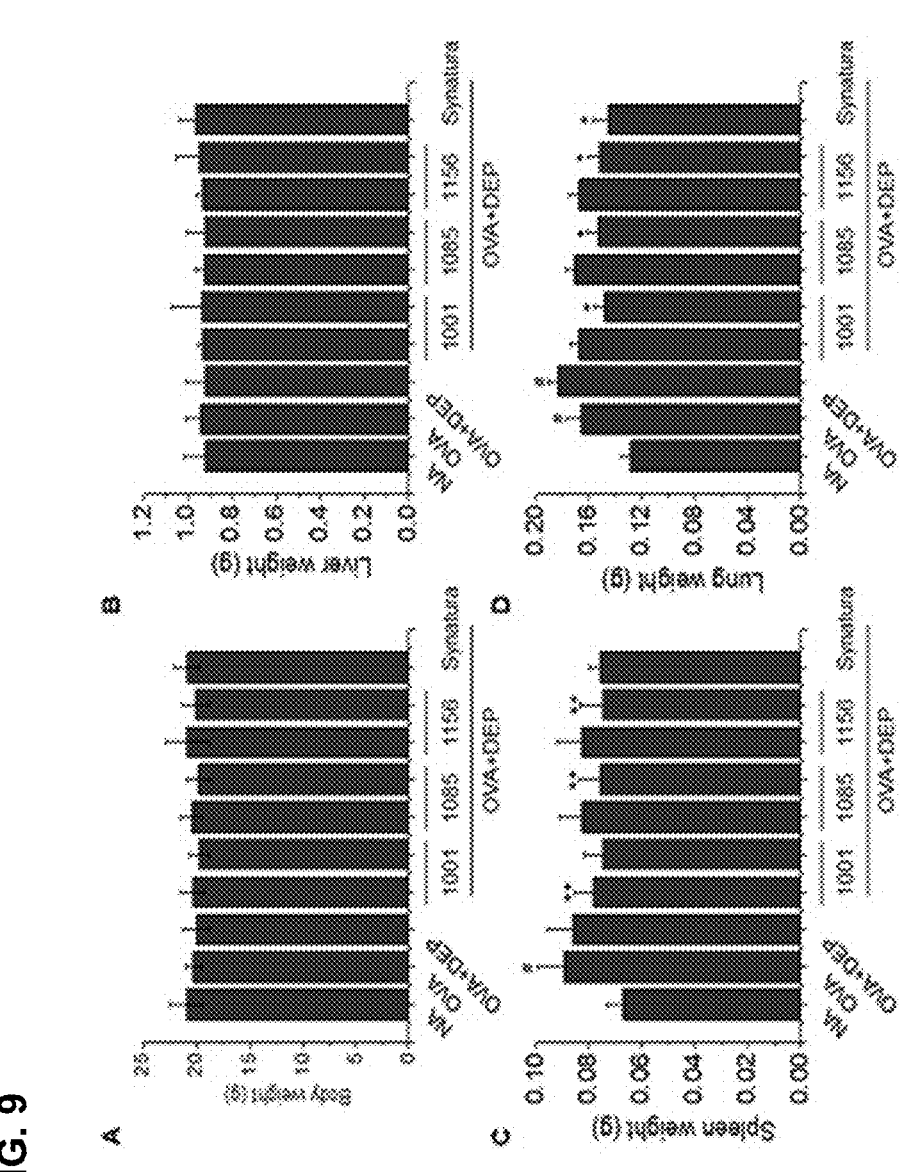
FIG. 9 is a graph showing body weight, and liver, spleen and lung weights after treatment with GCWB1001, GCWB1085 and GCWB1156 strains in a chronic respiratory disease animal model (Experimental Example 3-3).

As shown in FIG. 8, both GCWB1001 and GCWB1085 strains significantly increased the excreted amount of phenol red after administration of $1 \times 10^9$ cfu.

Overall, the strains of the present disclosure reduce the number of coughs and increase the expectorant action, thereby improving the symptoms of respiratory diseases.

Experiment Example 3: Analysis of Lung Function Alleviating Effect in Chronic Respiratory Disease Animal Model (In Vivo Assay)

3-1) Experimental Conditions and Breeding Conditions

Experimental animals were supplied with 6-week-old male BALB/c mice (body weight: 20±2 g) from Samtako Co., Ltd., and acclimatized for 7 days or more in an animal breeding room at a temperature of 23±1° C., relative humidity of 55±15%, and illuminance of 300 to 500 Lux with brightness adjusted at intervals of 12 hours. Thereafter, only normal animals were used for the experiment by observing the visual symptoms, and solid feed for laboratory animals (Samtako Co., Ltd.) and water were freely fed. All animal experiments were performed with the approval of the Laboratory Animal Ethics Committee of Korea International University, and performed according to the guidelines of the US National Institutes of Health (NIH publication No. 86-23, revised 1985).

3-2) Establishment of Chronic Respiratory Disease Animal Model and Administration of Experimental Materials Male 6-week-old BALB/c mice were intraperitoneally administered with 100 µg of ovalbumin (OVA) in a 1:1 mixture of 200 µl of aluminum hydroxide (Al(OH)$_3$) and saline once on Day 1 and Day 12 (Sensitization), respectively. On Days 19 and 20 of the experiment starting, 50 µg of OVA (Challenge) was intranasally administered once. Finally, after the OVA was administered intranasally (Day 20), 400 µg of diesel exhaust particles (DEP) were intranasally administered three times at 3-hour intervals, and the experiment was terminated on Day 21.

After 24 hours after the last sample administration, urethane (Sigma-Aldrich, UK, USA) was administered intraperitoneally (0.020 ml/g weight) to be anesthetized, and then a bronchoalveolar lavage fluid (BALF) was obtained. The strains of the present disclosure were orally administered once daily for Day 0 to Day 20. GCWB1001, GCWB1085, and GCWB1156 samples were orally administered at $1 \times 10^7$ cfu and $1 \times 10^9$ cfu per animal, respectively. Synatura (200 mg/kg) was used as a positive control, and the number of animals in each experimental group was 8 (n=8) (Table 9).

TABLE 9

| No. | Experimental group (n = 8) | Concentration |
|---|---|---|
| 1 | NA (control) | — |
| 2 | OVA (Ovalbumin) | 100 µg |
| 3 | OVA + DEP(Diesel exhaust particles) | 400 µg |
| 4 | OVA + DEP + GCWB1001 | $1 \times 10^7$ cfu |
| 5 | OVA + DEP + GCWB1001 | $1 \times 10^9$ cfu |
| 6 | OVA + DEP + GCWB1085 | $1 \times 10^7$ cfu |
| 7 | OVA + DEP + GCWB1085 | $1 \times 10^9$ cfu |
| 8 | OVA + DEP + GCWB1156 | $1 \times 10^7$ cfu |
| 9 | OVA + DEP + GCWB1156 | $1 \times 10^9$ cfu |
| 10 | OVA + DEP + Synatura | 200 mg/kg |

3-3) Measurement of Body Weight and Organ Weight

After 24 hours of the last sample administration, urethane (Sigma-Aldrich, UK, USA) was administered intraperitoneally (0.020 ml/g weight) to be anesthetized, a bronchoalveolar lavage fluid (BALF) was obtained, and then the lung was extracted and weighed. In addition, the body weight, and the liver and spleen weights were additionally measured.

There was no change in body weight in all of the groups, and the lung weight was increased in OVA and OVA+DEP treated groups compared to an untreated group, and in the GCWB1001 ($1 \times 10^9$ cfu), GCWB1085 ($1 \times 10^9$ cfu), GCWB1156 ($1 \times 10^9$ cfu), and Synatura treated groups, the weight of the lung tissue increased by OVA+DEP treatment was significantly reduced. Even in the spleen, in GCWB1001 ($1 \times 10^7$ cfu), GCWB1085 ($1 \times 10^9$ cfu), and GCWB1156 ($1 \times 10^9$ cfu), the weights of spleen and lung tissues increased by OVA+DEP treatment were significantly decreased.

3-4) Evaluation of Alleviating Lung Function of Strains of the Present Disclosure in Chronic Respiratory Disease Animal Model—Analysis of Bronchoalveolar Cell Fluid After 24 hours of the last sample administration, urethane (Sigma-Aldrich, UK, USA) was administered intraperitoneally (0.020 ml/g weight) to be anesthetized, a bronchoalveolar lavage fluid (BALF) was obtained, and then immune cell profiles (Total cells, Macrophages, Eosinophils, Neutrophils, Lymphocytes) were measured in the BALF.

Figure 10:
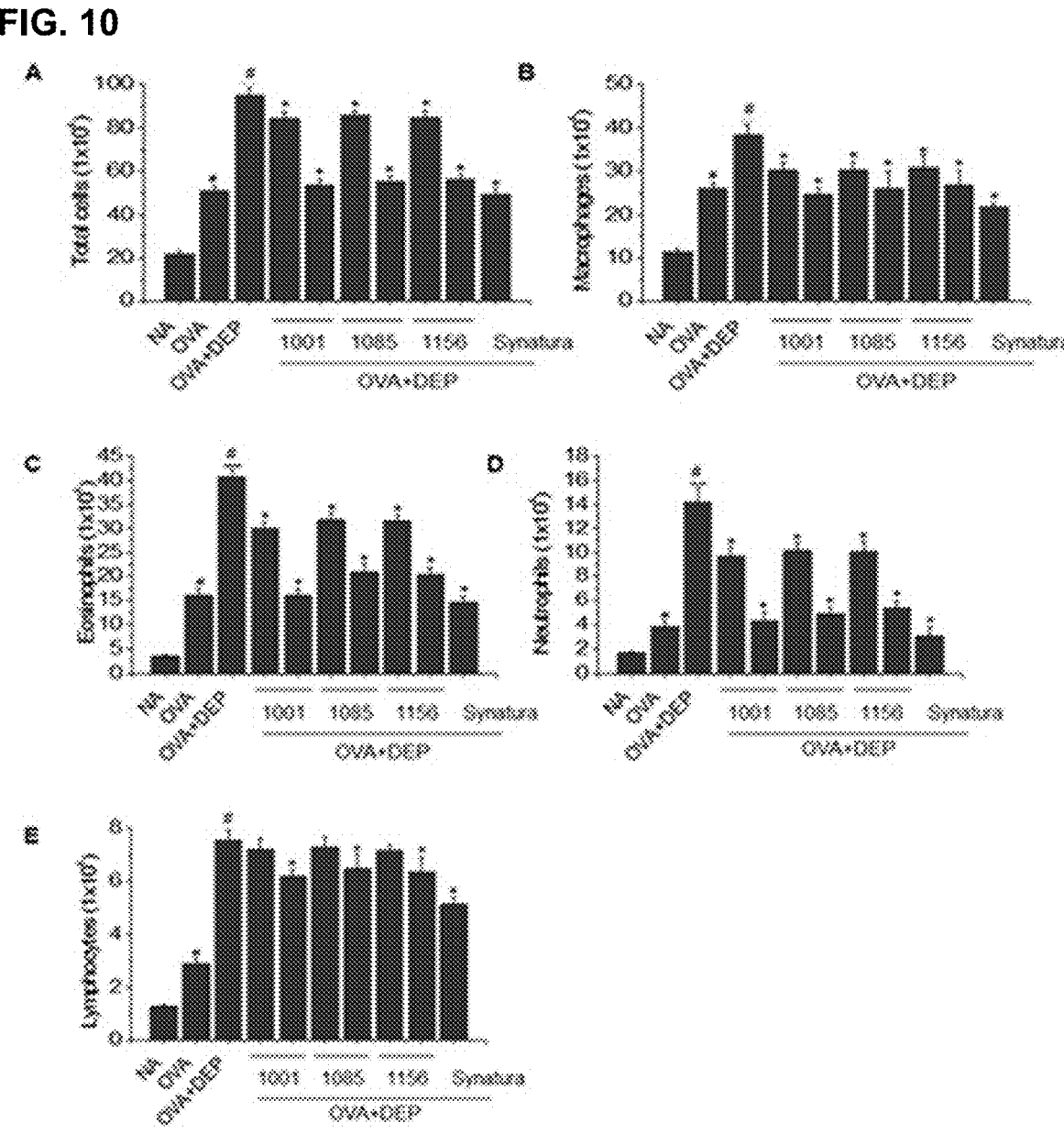
FIG. 10 is a graph showing the result of measuring the number of various immune cells in a Broncoalveolar lavage fluid (BALF) after treatment with GCWB1001, GCWB1085 and GCWB1156 strains from an animal model of chronic respiratory disease (Experimental Example 3-4).

According to FIG. 10, compared with a normal group, the number of all immune cells measured in an OVA-treated group was significantly increased, and compared with the OVA-treated group, the number of immune cells including the total number of cells was significantly increased even in the OVA+DEP-treated group. However, the number of immune cells increased by OVA+DEP treatment was significantly decreased in the samples of the groups treated with GCWB1001, GCWB1085, GCWB1156, and Synatura.

In particular, when each strain was treated with $1 \times 10^9$ cfu, the cell number of all immune cells showed a decrease comparable to that of a positive control, synatura, and even when $1 \times 10^7$ cfu was treated, the number (Total cells, Macrophages, Eosinophils, Neutrophils) of cells other than Lymphocytes was effectively reduced.

Accordingly, since the strains of the present disclosure reduce the infiltration of immune cells into the lung tissue, these may prevent the progression of respiratory diseases.

3-5) Evaluation of Alleviating Lung Function of Strains of the Present Disclosure in Chronic Respiratory Disease Animal Model—Measurement of OVA-Specific IgE (BALF, Serum)

After 24 hours of the last sample administration, urethane (Sigma-Aldrich, UK, USA) was administered intraperitoneally (0.020 ml/g weight) to be anesthetized, a bronchoalveolar lavage fluid (BALF) and a serum were obtained, and then the amount of OVA-specific-IgE, which is an indicator of an allergic reaction as a type of inflammatory response, was measured.

Figure 11:
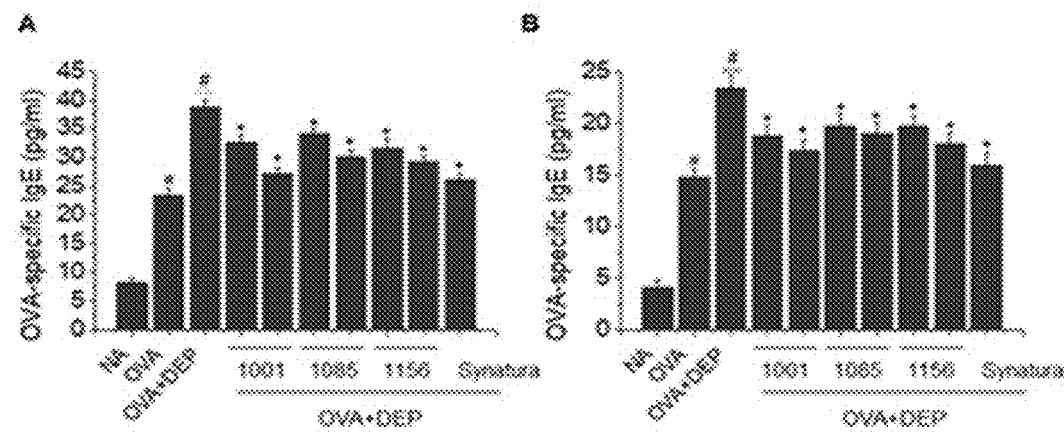
FIG. 11 is a graph of measuring the amount of OVA-specific IgE in a Broncoalveolar lavage fluid (BALF) after treatment with GCWB1001, GCWB1085 and GCWB1156 strains in a chronic respiratory disease animal model (Experimental Example 3-5).

As shown in FIG. 11, OVA-specific-IgE was significantly increased in BALF (FIG. 11A) and serum (FIG. 11B) of the OVA-treated group compared to the normal group, and the OVA-specific-IgE was significantly increased in the OVA+DEP-treated group compared to the OVA-treated group. OVA-specific-IgE increased by OVA+DEP treatment was significantly decreased in the samples, GCWB1001 ($1 \times 10^7$, $1 \times 10^9$ cfu), GCWB1085 ($1 \times 10^7$, $1 \times 10^9$ cfu), GCWB1156 ($1 \times 10^7$, $1 \times 10^9$ cfu), and Synatura-treated groups. Therefore, the strains of the present disclosure may reduce pulmonary and systemic allergic reactions, which are indicators of inflammatory responses.

3-6) Evaluation of Alleviating Lung Function of Strains of the Present Disclosure in Chronic Respiratory Disease Animal Model—Measurement of Cytokines (TNF-Alpha, IL-6, IL-1Beta, IL-4, IL-13, MCP-1, and IFN-Gamma) in BALF After 24 hours of the last sample administration, urethane (Sigma-Aldrich, UK, USA) was administered intraperitoneally (0.020 ml/g weight) to be anesthetized, and then cytokines (TNF-alpha, IL-6, IL-1beta, IL-4, IL-13, MCP-1, and IFN-gamma) in BALF were measured using an ELISA kit (R&D system USA).

TNF-alpha, IL-6, IL-1beta, IL-4, IL-13, and MCP-1 were significantly increased in the OVA-treated group as compared to the normal group, and TNF-alpha, IL-6, IL-1beta, IL-13, and MCP-1 were significantly increased in the OVA+DEP-treated group as compared to the OVA-treated group. TNF-alpha, IL-6, IL-1beta, IL-4, IL-13, and MCP-1 increased by OVA+DEP treatment were significantly decreased in the strains of the present disclosure, GCWB1001 ($1\times10^7$, $1\times10^9$ cfu), GCWB1085 ($1\times10^7$, $1\times10^9$ cfu), GCWB1156 ($1\times10^7$, $1\times10^9$ cfu), and Synatura-treated groups (FIG. 12A~FIG. 12D).

Figure 12:
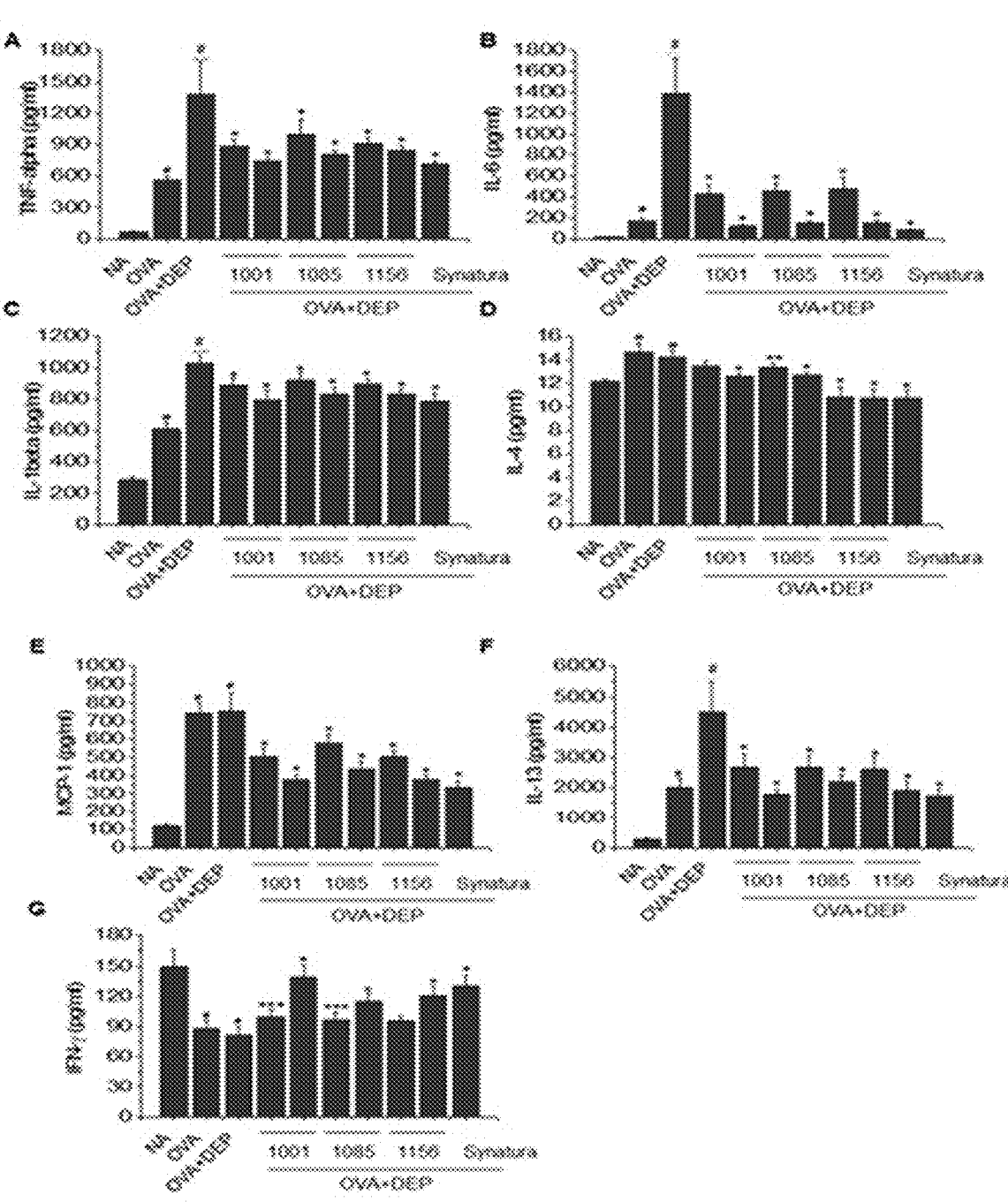
FIG. 12 is a graph of measuring the amounts of cytokines (TNF-alpha, IL-6, IL-1beta, IL-4, IL-13, and MCP-1) in a Broncoalveolar lavage fluid (BALF) after treatment with GCWB1001, GCWB1085 and GCWB1156 strains in a chronic respiratory disease animal model (Experimental Example 3-6).

In addition, the amount of IFN-gamma was decreased in the OVA+DEP treated group, but significantly increased in GCWB1001 ($1\times10^7$, $1\times10^9$ cfu), GCWB1085 ($1\times10^7$, $1\times10^9$ cfu), GCWB1156 ($1\times10^7$, $1\times10^9$ cfu), and Synatura-treated groups (FIG. 12G).

Therefore, since the strains of the present disclosure reduce pro-inflammatory cytokines in the lung and increase anti-inflammatory cytokines and thus may reduce the inflammatory response in the lung tissue, these may prevent the progression of respiratory diseases.

3-7) Evaluation of Alleviating Lung Function of Strains of the Present Disclosure in Chronic Respiratory Disease Animal Model—Histological Examination (H&E Staining)

The left lobe lung tissue was fixed in 10% formalin for 24 hours, and then a paraffin block was prepared, cut to a thickness of 4 μm, and then subjected to H&E staining. After an image was obtained with an optical microscope, the degree of inflammation was measured.

The infiltration of the inflammatory cells was significantly increased in the OVA-treated group compared to the normal group, and the infiltration of the inflammatory cells was significantly increased in the OVA+DEP-treated group compared to the OVA-treated group.

Figure 13:
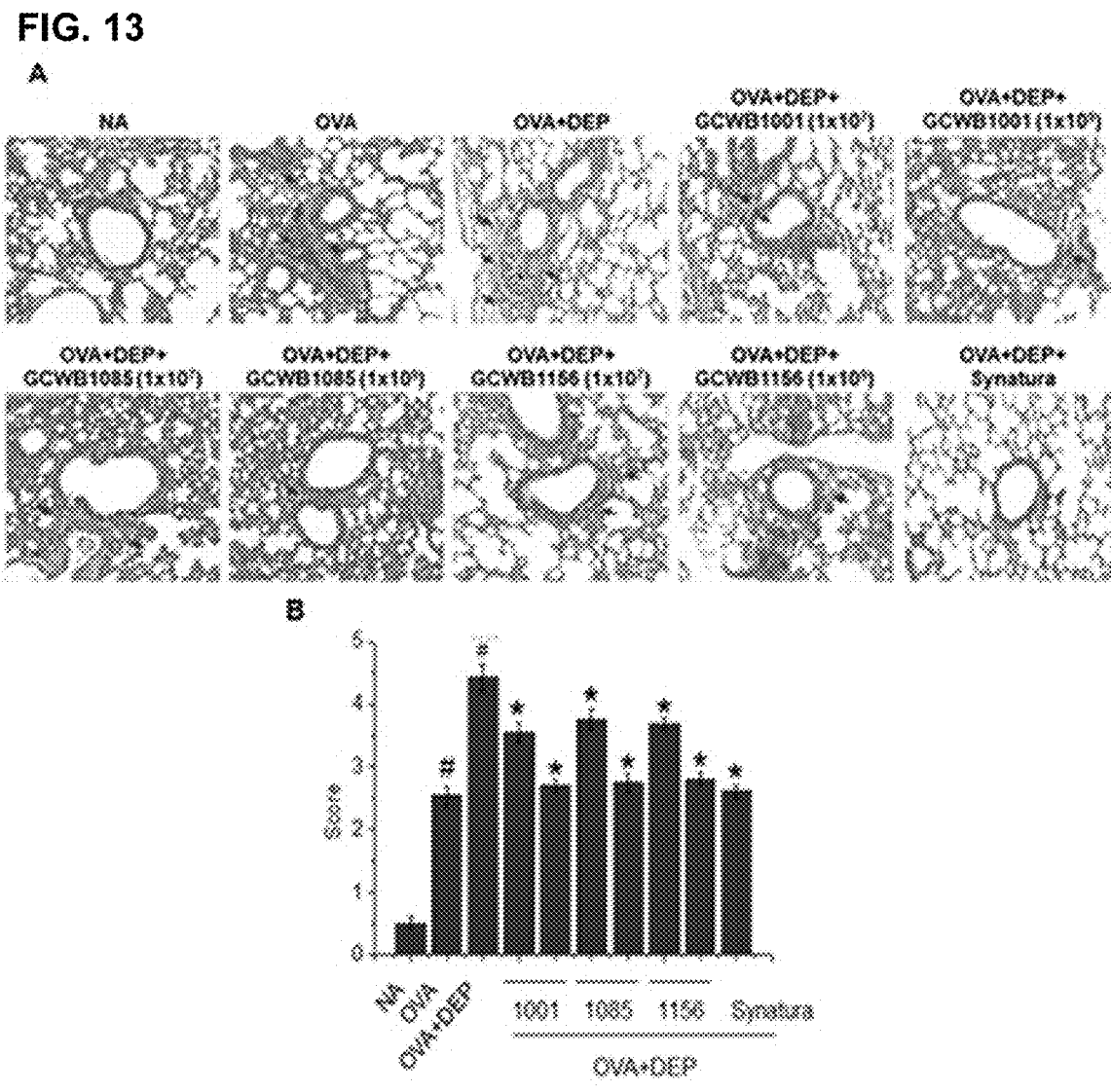
FIG. 13 is a lung tissue photograph and graph obtained by staining inflammatory cells penetrating into lung tissue after treatment with GCWB1001, GCWB1085 and GCWB1156 strains in a chronic respiratory disease animal model (Experimental Examples 3-7).

The infiltration of the inflammatory cells increased by OVA+DEP treatment was significantly decreased in the strains of the present disclosure, GCWB1001 ($1\times10^7$, $1\times10^9$ cfu), GCWB1085 ($1\times10^7$, $1\times10^9$ cfu), GCWB1156 ($1\times10^7$, $1\times10^9$ cfu), and Synatura-treated groups (FIG. 13).

Accordingly, since the strains of the present disclosure block the infiltration of the inflammatory cells into the lung tissue and thus reduce the inflammation responses in the lung tissue, these may prevent the progression of respiratory diseases.

3-8) Evaluation of Alleviating Lung Function of Strains of the Present Disclosure in Chronic Respiratory Disease Animal Model—Histological Examination (Alcian Blue-PAS Stain)

In order to confirm whether the strains of the present disclosure actually inhibited the production of mucous proteins in the lung tissue, the lung tissue was stained by an alcian blue-PAS staining method for staining glycogen and mucin.

Figure 14:
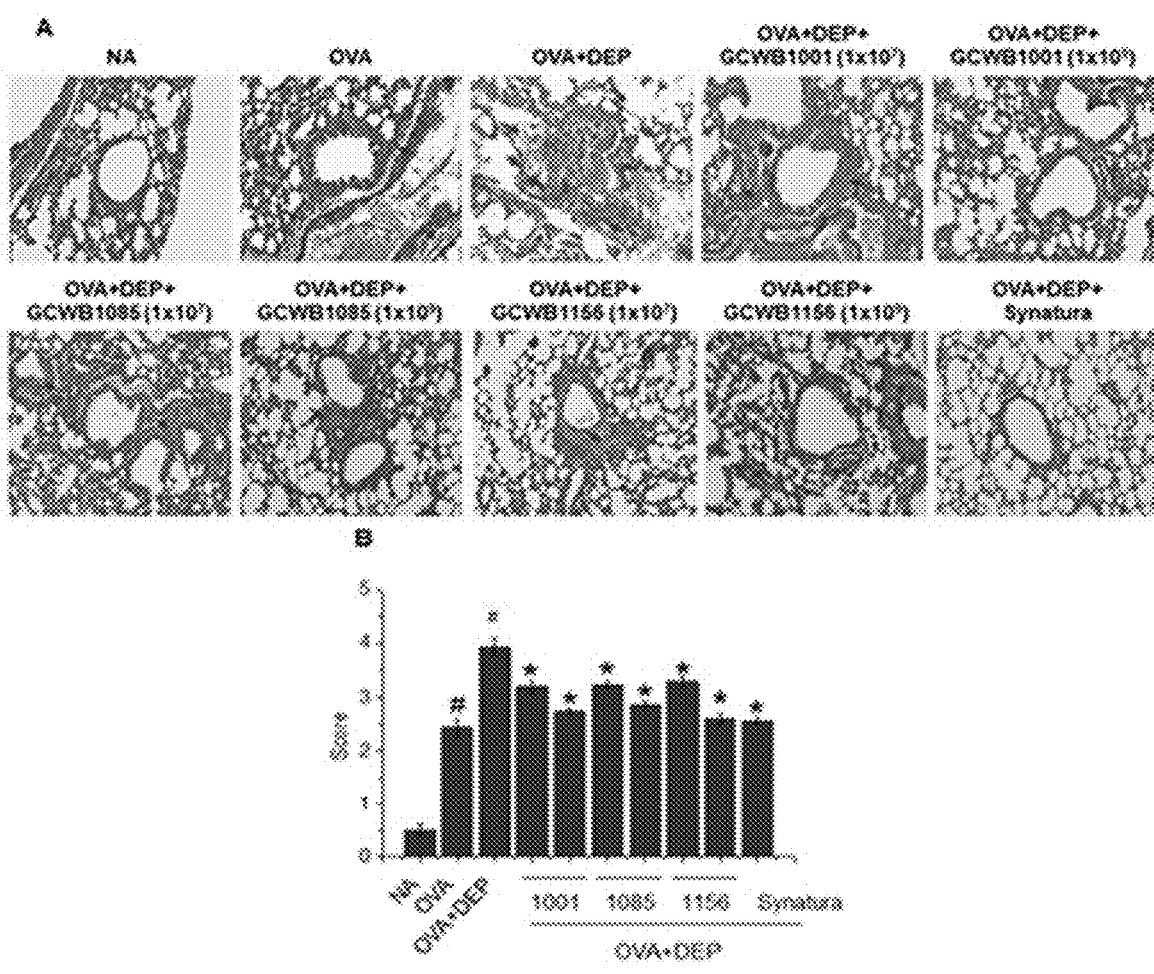
FIG. 14 is a lung tissue photograph and graph obtained by staining a mucous protein after treatment with GCWB1001, GCWB1085 and GCWB1156 strains in a chronic respiratory disease animal model (Experimental Examples 3-8).

FIG. 14 is a photograph of an actual stained tissue, in which the production of mucous proteins in the alveoli was significantly increased in the OVA-treated group compared to the normal group, and the production of the mucous proteins was significantly increased in the OVA+DEP treated group compared to the OVA treated group. The production of the mucous proteins increased by OVA+DEP treatment was significantly decreased in the samples, GCWB1001 ($1\times10^7$, $1\times10^9$ cfu), GCWB1085 ($1\times10^7$, $1\times10^9$ cfu), GCWB1156 ($1\times10^7$, $1\times10^9$ cfu), and Synatura-treated groups (FIG. 14).

Therefore, since the strains of the present disclosure reduce the mucus in the alveoli, it may prevent the deterioration of advanced stage of respiratory diseases into pulmonary fibrosis and the like.

3-9) Evaluation of Alleviating Lung Function of Strains of the Present Disclosure in Chronic Respiratory Disease Animal Model—Caspase 3 Activity and Total Collagen Content In order to confirm whether the strains of the present disclosure actually reduced apoptosis in the lung tissue and improved lung damage, caspase 3 activity and total collagen content in the lung tissue were measured.

Figure 15:
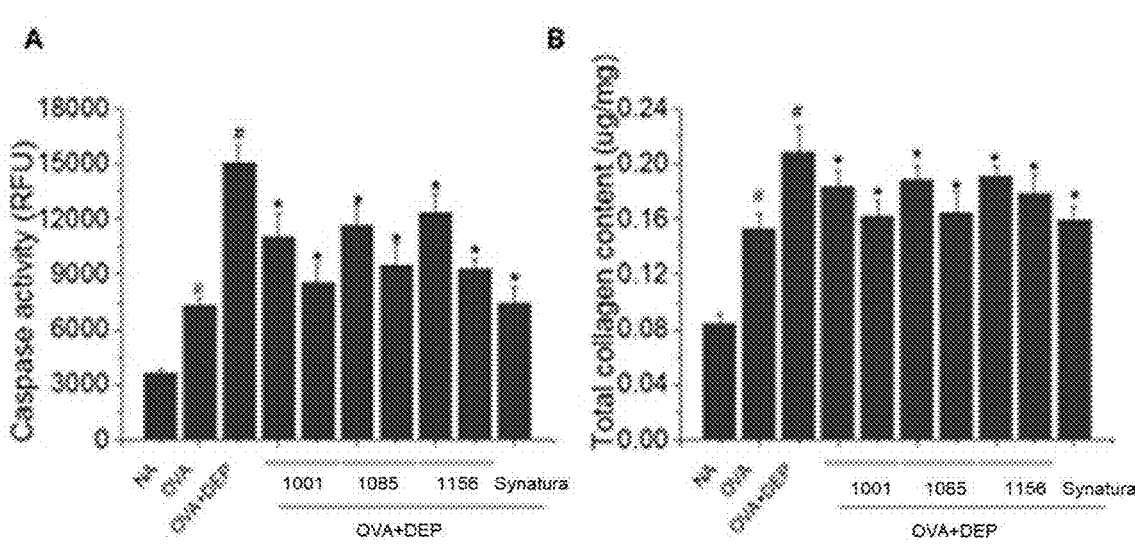
FIG. 15 is a graph showing caspase 3 activity and total collagen content in lung tissue after treatment with GCWB1001, GCWB1085 and GCWB1156 strains in a chronic respiratory disease animal model (Experimental Examples 3-9).

According to FIG. 15, the caspase-3 activity and the collagen content were significantly increased in the OVA-treated group compared to the normal group, and the caspase-3 activity and the collagen content were significantly increased in the OVA+DEP-treated group compared to the OVA-treated group. Both the caspase-3 activity and the collagen content increased by OVA+DEP treatment were significantly decreased in the strains of the present disclosure, GCWB1001 ($1\times10^7$, $1\times10^9$ cfu), GCWB1085 ($1\times10^7$, $1\times10^9$ cfu), GCWB1156 ($1\times10^7$, $1\times10^9$ cfu), and Synatura-treated groups (FIG. 15).

Therefore, the strains of the present disclosure may prevent pulmonary fibrosis, which is the deterioration of advanced stage of respiratory diseases, by not only reducing the apoptosis factor but also reducing the collagen content.

3-10) Evaluation of Alleviating Lung Function of Strains of the Present Disclosure in Chronic Respiratory Disease Animal Model—Analysis of MMP9 Activity Proteins isolated by 10% SDS-PAGE electrophoresis containing 0.2% gelatin in a bronchoalveolar lavage fluid (BALF) were stained with 0.25% Coomassie Brilliant Blue G250 (Sigma Chemical Co., St. Louis, MO, USA) and then the MMP-9 enzyme activity was measured.

Figure 16:
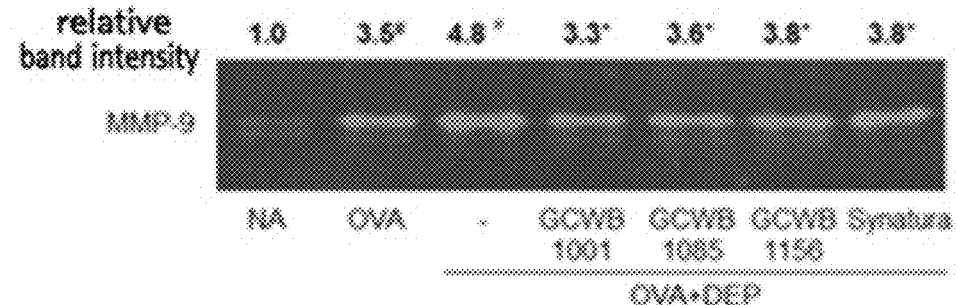
FIG. 16 is a photograph of analyzing MMP-9 activity in lung tissue after treatment with GCWB1001, GCWB1085 and GCWB1156 strains in a chronic respiratory disease animal model (Experimental Examples 3-10).

According to FIG. 16, the MMP-9 activity was significantly increased in the OVA-treated group compared to the normal group, and the MMP-9 activity was significantly increased in the OVA+DEP-treated group compared to the OVA-treated group. The MMP-9 activity increased by OVA+DEP treatment was significantly reduced in the strains of the present disclosure, GCWB1001 ($1\times10^9$ cfu), GCWB1085 ($1\times10^9$ cfu), GCWB1156 ($1\times10^9$ cfu), and Synatura treated groups.

Therefore, since the strains of the present disclosure can prevent the deposition of inflammatory cells in the lung tissue, it may prevent inflammation in the lung tissue and various complications caused by inflammation.

The invention claimed is:

1. A method for treating an inflammatory disease or a respiratory disease in a subject in need thereof, comprising administering to the subject an effective amount of a pharmaceutical composition comprising a *Lactobacillus plantarum* GCWB1001 strain deposited as accession number KCCM12698P, wherein the pharmaceutical composition is selected from the group consisting of spray-dried strain, freeze-dried strain, vacuum dried strain, drum dried strain, crushed strain, a culture of the strain, a concentrate of the culture, a paste of the culture, a dilution of the culture, and a combination thereof.

2. The method of claim 1, wherein the respiratory disease is caused by fine dust, viral infection, or inflammation.

3. The method of claim 1, wherein the respiratory disease is selected from the group consisting of respiratory inflammatory lung disease, asthma, bronchiectasis, idiopathic pulmonary fibrosis, chronic obstructive pulmonary disease (COPD), cystic fibrosis, emphysema, sequelae of pulmonary tuberculosis, allergic rhinitis, lower respiratory tract infection, bronchiolitis, acute upper respiratory tract infection, allergic lung disease, bronchiectasis, pneumonia, acute and chronic bronchitis, sinusitis, pharyngitis, tonsillitis, and laryngitis.

4. The method of claim 2, wherein the viral infection is caused by virus selected from the group consisting of adenovirus, vaccinia virus, herpes simplex virus, parainfluenza virus, rhinovirus, varicella Zoster Virus, measle virus, respiratory syncytial virus, Dengue virus, human immunodeficiency virus (HIV), influenza virus, coronavirus, severe acute respiratory syndrome associated virus (SARS-associated virus) and middle east respiratory syndrome coronavirus (MERS-CoV).

5. A method for alleviating an inflammatory disease or a respiratory disease in a subject in need thereof, comprising administering to the subject a probiotic composition comprising a *Lactobacillus plantarum* GCWB1001 strain deposited as accession number KCCM12698P.

6. The method of claim 5, wherein the respiratory disease is caused by fine dust, viral infection and pneumonia.

7. The method of claim 5, wherein the probiotic composition is antitussive or is an expectorant.

8. The method of claim 5, wherein the probiotic composition reduces inflammatory response in lung tissue.

9. The method of claim 5, wherein the probiotic composition reduces allergic reactions in lungs or systemic allergic reactions.

10. The method of claim 5, wherein the probiotic composition inhibits pulmonary fibrosis.

* * * * *